(12) United States Patent
Fujita et al.

(10) Patent No.: US 7,681,451 B2
(45) Date of Patent: Mar. 23, 2010

(54) PASSAGE DETECTION APPARATUS OF OBJECT

(75) Inventors: Shuhei Fujita, Nagoya (JP); Kunihiko Yoshioka, Nagoya (JP); Takao Ohnishi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 317 days.

(21) Appl. No.: 11/775,427

(22) Filed: Jul. 10, 2007

(65) Prior Publication Data
US 2008/0047349 A1   Feb. 28, 2008

(30) Foreign Application Priority Data
Jul. 11, 2006   (JP) .............................. 2006-190018

(51) Int. Cl.
*G01N 9/24* (2006.01)

(52) U.S. Cl. .............................. 73/617; 73/584; 73/609

(58) Field of Classification Search .................... 73/617, 73/584, 609, 622, 644, 579
See application file for complete search history.

(56) References Cited

U.S. PATENT DOCUMENTS 5,107,844 A * 4/1992 Kami et al. ................. 600/463

6,684,132 B2 * 1/2004 Wakui et al. ................. 700/280
6,710,516 B1 * 3/2004 Tamai ..................... 310/323.13

FOREIGN PATENT DOCUMENTS

| JP | 2001-124789 | 5/2001 |
| JP | 2001-186881 | 7/2001 |
| KR | 2007020787 | * 2/2007 |

* cited by examiner

*Primary Examiner*—Hezron Williams
*Assistant Examiner*—J M Saint Surin
(74) *Attorney, Agent, or Firm*—Burr & Brown

(57) ABSTRACT

Disclosed herein is a passage detection apparatus capable of detecting a passage of an object in a specific space. The passage detection apparatus includes a transmitting device, a receiving device, and a shielding member. The transmitting device is provided with a vibration generating source. The receiving device is arranged at the position corresponding to the transmitting device across the specific space. The shielding member has a through-hole, and is arranged so as to be interposed between the transmitting device and the receiving device. The vibration transmitted from the transmitting device reaches the receiving device via the through-hole and a passage route of the object. On the other hand, the reception of the vibration, reflected in the specific space, by the receiving device is suppressed by the shielding member.

7 Claims, 24 Drawing Sheets

PASSAGE DETECTION APPARATUS OF OBJECT

BACKGROUND OF THE INVENTION

1. Field of the Invention

The present invention relates to a passage detection apparatus of an object that can detect a passage of an object in a specific space.

2. Description of the Related Art

For example, various methods of manufacturing a so-called DNA chip (a DNA micro array) are well known. The DNA chip is generally constructed by arraying and fixing micro spots of several thousand to ten thousand or more kinds of different DNA pieces on a substrate, such as microscope slide glass, with high density.

As examples of the DNA chip manufacturing methods, there have been proposed methods of manufacturing a DNA chip using a micropipette for ejecting drops having micro volume (for example, see the following Patent References 1 and 2). The micropipette includes an injection port for injecting a sample solution from the outside, a cavity for allowing the sample solution injected from the injection port to be filled therein, an ejection port communicating with the cavity, and a piezoelectric/electrostrictive element constructed to change the interior volume of the cavity such that the sample solution can be ejected from the ejection port.

According to the above-described DNA chip manufacturing methods, the interior volume of the cavity is changed by the driving operation of the piezoelectric/electrostrictive element. As the interior volume of the cavity is changed, the sample solution moves from the cavity to the ejection port in the form of a streamline flow. That is, a predetermined amount of the sample solution is delivered from the cavity to the ejection port. As the predetermined amount of the sample solution is ejected from the ejection port, micro drops of the sample solution are generated. The micro drops of the sample solution ejected from the micropipette are attached to the substrate, and the micro drops are arrayed and fixed on the substrate as micro spots. In this way, the DNA chip is manufactured.

An apparatus constructed to eject a micro object (hereinafter, simply referred to as a "micro object ejection apparatus"), such as the micropipette used in the DNA chip manufacturing method as described above, may be utilized in various technical fields.

[Patent Reference 1] Japanese Unexamined Patent Publication No. 2001-124789

[Patent Reference 2] Japanese Unexamined Patent Publication No. 2001-186881

The micro object ejection apparatus of this type has been required to more correctly detect the passage of the object having more micro size. This can be achieved by enhancing an S/N ratio in the detection of a passage of an object.

SUMMARY OF THE INVENTION

A passage detection apparatus of an object (hereinafter simply referred to as "passage detection apparatus") is configured to detect a passage of an object in a specific space. The passage detection apparatus includes a transmitting device, receiving device, and shielding member. The feature of the present invention is such that the passage detection apparatus includes the shielding member.

The transmitting device is provided with a vibration generating source. The receiving device is arranged at the position corresponding to the transmitting device across the specific space. The receiving device is configured to generate an output according to a vibration that is generated from the transmitting device to propagate through a medium in the specific space. There is no special limitation upon the type of a material composing the medium. For example, gas such as air, liquid such as water or oil, etc. can be used for the medium.

The shielding member is interposed between the transmitting device and the receiving device. The shielding member is formed with a through-hole. The through-hole is formed between the transmitting device and the receiving device so as to face a route through which the object passes. tk In the passage detection apparatus according to the present invention having the aforesaid configuration, a direct propagating route of the vibration is formed that reaches the receiving device from the transmitting device through the through-hole of the shielding member and the passage route of the object. On the other hand, the reception of the vibration, which is multiplied and reflected in the specific space, by the receiving device can now be suppressed by the shielding member. Specifically, the shielding member provides an effect of shielding the receiving device from the multiply reflected vibration.

This configuration enhances the S/N ratio in the detection of the passage of the object. Accordingly, an object having more micro size can more correctly be detected.

The shielding member may be configured to have an inclined face in which the direction crossing the direct vibration propagating direction is defined as the normal. The direct vibration propagating direction means the direction linking the transmitting device and the receiving device. In other words, the direct vibration propagating direction is the vibration propagating direction when the vibration generated from the transmitting device directly reaches the receiving device through the through-hole without being (multiply) reflected in the specific space. It is preferable that the angle made by the direct vibration propagating direction and the inclined face is 40 to 50 degrees.

In the above-described configuration, the vibration multiply reflected in the specific space is reflected by the inclined face of the shielding member. Thus, the propagating direction of the reflected vibration can be greatly deviated from the direct vibration propagating direction that links the through-hole and the receiving device. Accordingly, the reception of the multiply reflected vibration by the receiving device can more effectively be suppressed.

This configuration enhances the S/N ratio in the detection of the passage of the object. Accordingly, an object having a more micro size can be more correctly detected.

On the assumption that the circle-equivalent diameter of the through-hole is defined as d1, the circle-equivalent diameter of the object is defined as d2, the average speed of the object at the through-hole is defined as v, and the cycle of the vibration is defined as T, the passage detection apparatus may be configured to satisfy the following inequalities:

$$d2^2/d1^2 \geq 0.6, (d1-d2)/v \geq 3T$$

The circle-equivalent diameter of the through-hole means the diameter of the circle having the area same as the area of the through-hole on a plane, in which the straight line (the line parallel to the direct vibration propagating direction) linking the transmitting device and the receiving device is defined as the normal, in the event that the through-hole is projected on the plane. The same is true for the circle-equivalent diameter of the object.

In this configuration, the state in which the through-hole and the object are overlapped with each other on the straight line continues for a period sufficient for the detection of the passage of the object, when the vibration passes through the through-hole. Therefore, the rate of change of the output signal from the receiving device caused by the passage of the object that is sufficient for the detection of the passage of the object can be produced. Accordingly, the detection of the passage of the object can more stably be performed with this configuration.

The passage detection apparatus may further be configured as follows. The receiving device includes a reference electrode that is set to a predetermined potential and a signal output electrode whose potential varies on the basis of the vibration or whether the object passes or not. The shielding member is also set to have the same potential as that of the reference electrode.

In this configuration, the reference electrode of the receiving device is set to a predetermined reference potential. The potential of the signal output electrode varies on the basis of whether the passage of the object is detected or not. The output signal from the receiving device can be obtained on the bases of the difference between the potential of the signal output electrode and the reference electrode potential, i.e., the voltage between the reference electrode and the signal output electrode.

Here, the potential of the shielding member is set to the potential of the reference electrode. Therefore, the shielding member provides not only the shielding effect to the multiply reflected vibration but also the shielding effect to electromagnetic noise.

This configuration enhances the S/N ratio in the detection of the passage of the object. Accordingly, an object having a more micro size can be more correctly detected with this configuration.

The passage detection apparatus may further be configured as follows. The transmitting device and the receiving device may be configured such that the resonant frequency of the transmitting device and the resonant frequency of the receiving device are generally the same in a first vibration mode, and the resonant frequency of the transmitting device and the resonant frequency of the receiving device are different from each other at a second vibration mode that is different from the first vibration mode.

In this configuration, the output from the receiving device on the basis of the vibration of the transmitting device other than the first vibration mode of the vibration generating source can be suppressed. With this, the S/N ratio in the detection of the passage of the object is more enhanced. Accordingly, the passage of a smaller object can be detected with higher precision with this configuration.

The passage detection apparatus may further include a determining section, and device noise reducing shield section and/or circuit noise reducing shield section. The determining section is configured to determine the passage of an object in the specific space on the basis of the output from the receiving device. The device noise reducing shield section is provided so as to cover the transmitting device and/or receiving device. The circuit noise reducing shield section is configured to cover the determining section for eliminating electrical noise applied to the determining section.

In this configuration, electrical noise is eliminated by the shield section. Therefore, the S/N ratio in the detection of the passage of the object is more enhanced. Accordingly, an object having a more micro size can be more correctly detected with this configuration.

The passage detection apparatus may further include a band-pass filter. The band-pass filter is configured to limit the frequency of the output from the receiving device to the band (specifically, the range ±10% of the desired resonant frequency) in the vicinity of the desired resonant frequency.

The band-pass filter may be interposed between the receiving device and the transmitting device. Alternatively, it can be provided to the determining section.

In this configuration, a mechanical noise is eliminated that is based upon ambient sound wave or the vibration or the like of an unnecessary mode other than the vibration of the desired mode corresponding to the desired resonant frequency. Accordingly, the S/N ratio for the detection of the passage of the object is enhanced. Consequently, an object having a more micro size can be detected with high precision.

The passage detection apparatus may further be configured as follows. The passage detection apparatus further includes an aperture plate. The aperture plate is a flat-plate member, and is arranged at an inlet-side end portion which is around the inlet for the object of the specific space so as to cross the passing direction of the object. The aperture plate is formed with an aperture, which is a through-hole through which the object can pass. The aperture is formed smaller than the size of the specific space at the section perpendicular to the passing direction of the object.

According to this configuration, the positional relationship between the specific space and the aperture is appropriately set, whereby the flight state (e.g., advancing direction, linearity, etc.) of the object in the specific space can be detected with more simplified construction of the apparatus.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which.

DETAILED DESCRIPTION OF THE INVENTION

Now, a preferred embodiment of the present invention will be described in detail with reference to the accompanying drawings.

<Construction of DNA Chip>

Figure 1:
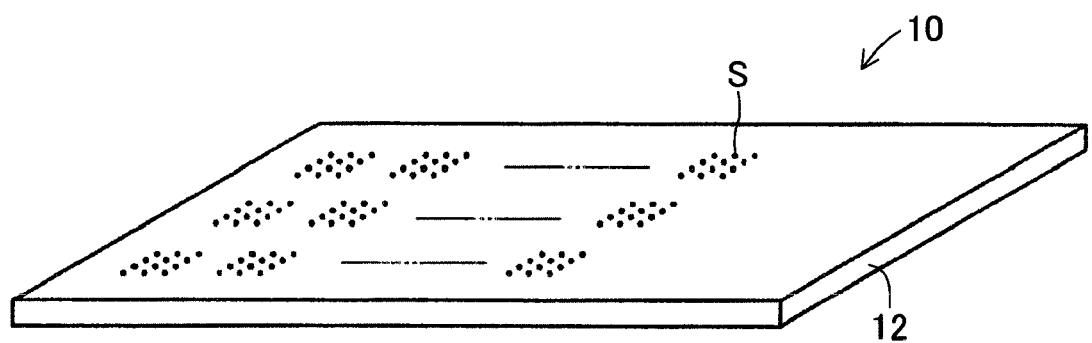
FIG. 1 is an external view (a perspective view) illustrating the general construction of a DNA chip.
Figure 2:
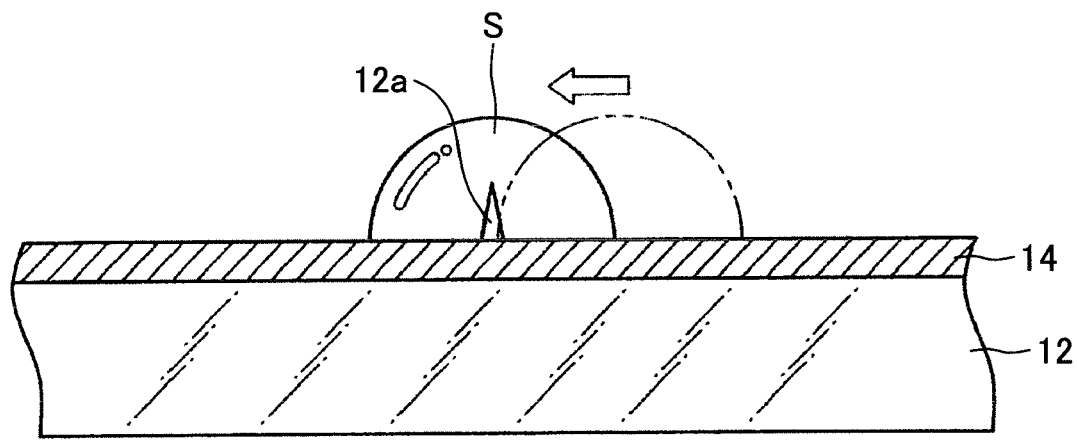
FIG. 2 is an enlarged sectional view of the DNA chip shown in FIG. 1.

FIG. 1 is an external view (a perspective view) illustrating the general construction of a DNA chip 10, and FIG. 2 is an enlarged sectional view of the DNA chip shown in FIG. 1.

As shown in FIG. 1, the DNA chip 10 is constructed by arranging plural micro spots S, which are formed by micro drops of a sample solution, on a DNA chip substrate 12, which is made of microscope slide glass.

As shown in FIG. 2, a protrusion 12a is formed on the DNA chip 12 at a predetermined position where the corresponding micro spot S is to be formed. When the corresponding micro spot S drops while deviating from the predetermined position, the protrusion 12a serves to compensate for the position deviation. Specifically, when a portion of the micro spot S is caught by the protrusion 12a (see a two-dot chain line), as shown in FIG. 2, the micro spot S is moved to the predetermined position by the surface tension of the micro spot S.

Also, a sample support layer 14, which is a poly-L-lysine layer having a hydrophilic property, is formed on the surface of the DNA chip substrate 12.

<Construction of Micropipette>

Figure 3:
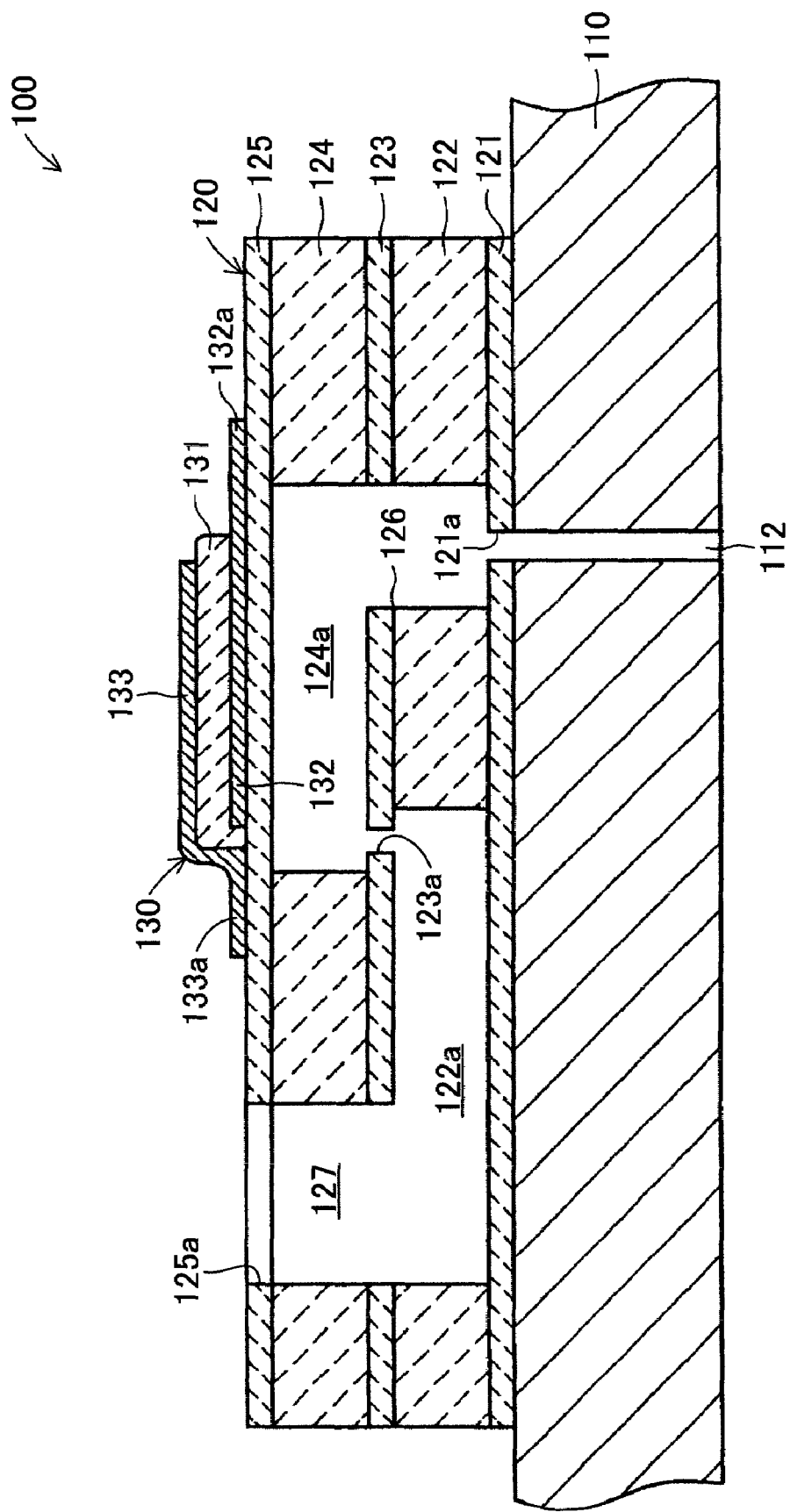
FIG. 3 is an enlarged sectional view showing a micropipette chip used for manufacturing the DNA chip shown in FIG. 1.
Figure 4:
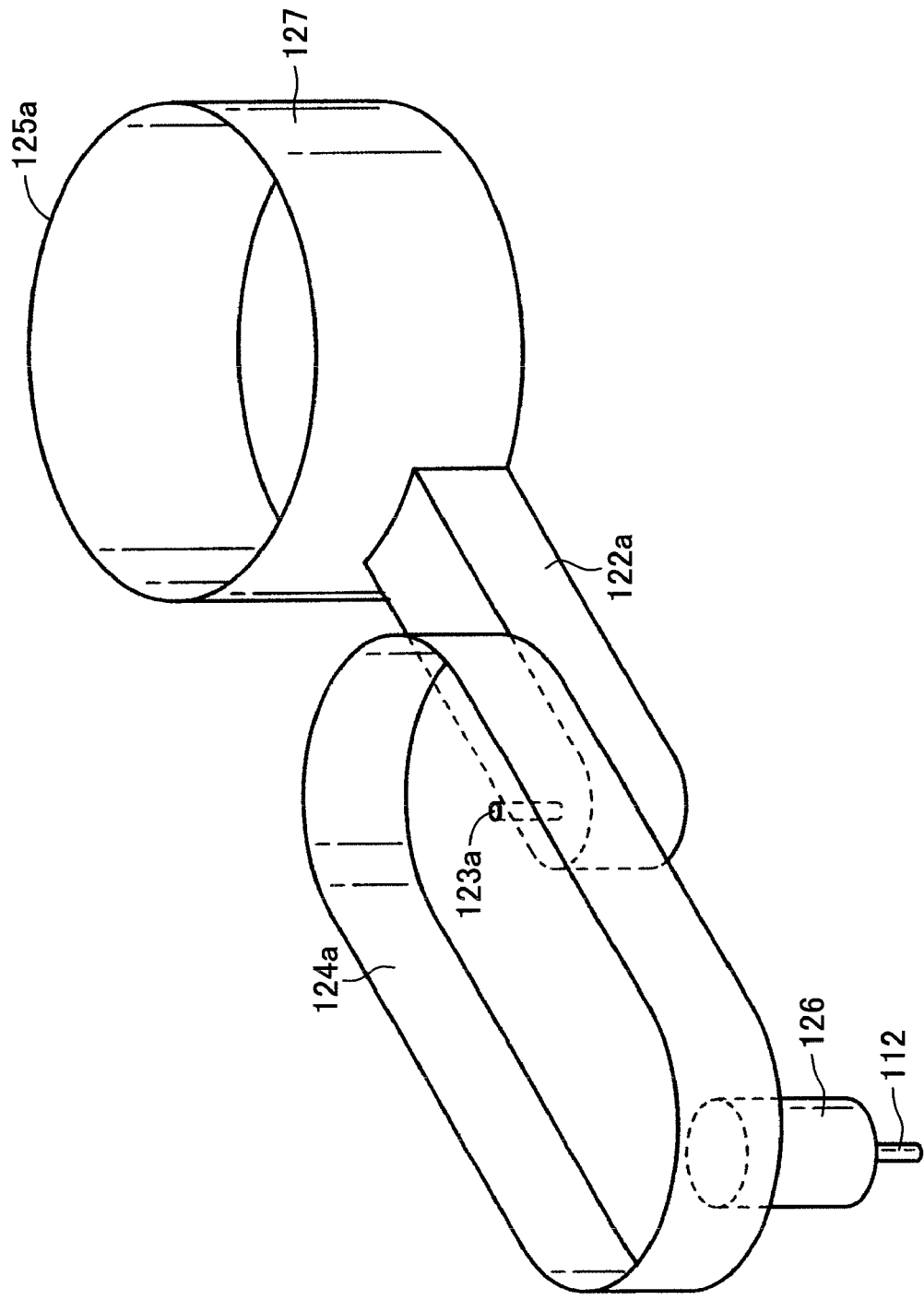
FIG. 4 is an enlarged and see-through perspective view illustrating the construction of a sample solution flow channel in the micropipette shown in FIG. 3.
Figure 5:
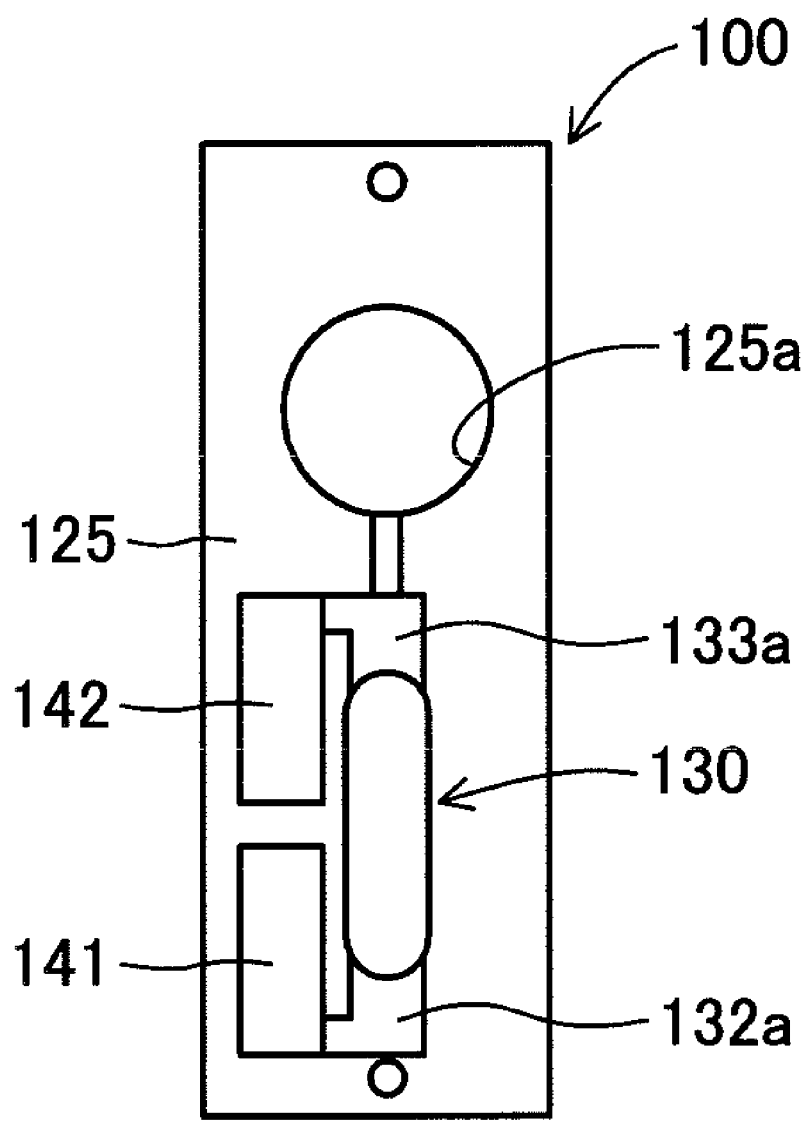
FIG. 5 is an enlarged plan view of the micropipette shown in FIG. 3.

Hereinafter, the structure of a micropipette, which is used to manufacture the above-described DNA chip 10, will be described in detail. FIG. 3 is an enlarged sectional view of the micropipette 100, FIG. 4 is a see-through perspective view illustrating the construction of a flow channel for a sample solution in the micropipette 100, and FIG. 5 is a plan view of the micropipette 100.

Referring to FIG. 3, the micropipette 100 includes a nozzle plate 110, a cavity unit 120 fixed to the upper surface of the nozzle plate 110, and an actuator unit 130 fixed to the upper surface of the cavity unit 120. In the nozzle plate 110 is formed a through-hole, i.e., a nozzle 112, through which the sample solution passes.

The nozzle plate 110 is formed from a thin ceramic plate. The material of the nozzle plate 110 includes, for example, zirconium oxide, aluminum oxide, magnesium oxide, aluminum nitride, and silicon nitride. Most preferably, a material mainly containing fully stabilized zirconium oxide or a material mainly containing partially stabilized zirconium oxide is used in terms of mechanical strength and a reaction to the material of a piezoelectric/electrostrictive film or an electrode film.

The cavity unit 120 includes a connection plate 121, a flow channel plate 122, an orifice plate 123, a cavity plate 124, and an injection port plate 125. The connection plate 121, the flow channel plate 122, the orifice plate 123, the cavity plate 124, and the injection port plate 125 are formed from a thin ceramic plate. The connection plate 121, the flow channel plate 122, the orifice plate 123, the cavity plate 124, the injection port plate 125, and the nozzle plate 110 are sintered while they are stacked in order on the nozzle plate 110. As a result, they are integrally formed at the nozzle plate 110.

The connection plate 121 is disposed at the connection between the cavity plate 120 and the nozzle plate 110 such that the connection plate 121 is joined to the upper surface of the nozzle plate 110. In the connection plate 121 is formed a through-hole having the same diameter as the nozzle 112, i.e., a nozzle communication hole 121a. The nozzle communication hole 121a is connected to a cavity 124a formed in the cavity plate 124 via a sample outlet hole 126. The sample outlet hole 126 is a through-hole having a diameter greater than that of the nozzle communication hole 121a. The sample outlet hole 126 is formed through the flow channel plate 122 and the orifice plate 123.

In the flow channel plate 122 is formed a sample supply channel 122a, through which the sample solution is supplied to the cavity 124a. The sample supply channel 122a and the cavity 124a are connected with each other via an orifice 123a, which is a through-hole, having a small diameter, formed in the orifice plate 123.

The injection port plate 125 is disposed at the uppermost layer of the cavity unit 120. In the injection port plate 125 is formed a sample injection port 125a, which is a through-hole for allowing the sample solution to be injected toward the sample supply channel 122a formed in the flow channel plate 122. The sample injection port 125a and the sample supply channel 122a formed in the flow channel plate 122 are connected with each other via a sample introduction hole 127, which is a through-hole. The sample introduction hole 127 is formed through the orifice plate 123 and the cavity plate 124.

As shown in FIG. 4, a sample solution flow channel is formed in the cavity unit 120 with the above-stated construction such that the sample solution flow channel extends from the sample injection port 125a to the nozzle 112. Specifically, the dimension of the orifice 123a is set such that, when the cavity 124a is pressurized, the sample solution in the cavity 124a does not flow backward to the sample supply channel 122a through the small-diameter orifice 123a but flows out toward the nozzle 112 through the sample outlet hole 126, and therefore, micro drops of the sample solution are ejected to the outside from the nozzle 112.

Referring back to FIG. 3, the actuator unit 130 includes a piezoelectric/electrostrictive layer 131, a lower electrode 132 fixed to the lower surface of the piezoelectric/electrostrictive layer 131, and an upper electrode 133 fixed to the upper surface of the piezoelectric/electrostrictive layer 131. The piezoelectric/electrostrictive layer 131 is disposed at a predetermined position corresponding to the cavity 124a (i.e., right above the cavity 124a). The lower electrode 132 is fixed to the upper surface of the injection port plate 125, and therefore, the actuator unit 130 is fixed to the upper surface of the cavity unit 120. The actuator unit 130 is constructed such that the actuator unit 130 changes the interior volume of the cavity 124a, when drive voltage is applied between the lower electrode 132 and the upper electrode 133, to eject a predetermined amount of the sample solution from the nozzle 112.

The lower electrode 132 is connected to a lower electrode wiring pattern 132a, which is a conductive film formed at the upper surface of the injection port plate 125. The upper electrode 133 is connected to an upper electrode wiring pattern 133a, which is a conductive film formed at the upper surface of the injection port plate 125.

As shown in FIG. 5, a lower electrode input terminal 141 is formed at the upper surface of the injection port plate 125. The lower electrode input terminal 141 is connected to the lower electrode wiring pattern 132a. Also, an upper electrode input terminal 142 is formed at the upper surface of the injection port plate 125. The upper electrode input terminal 142 is connected to the upper electrode wiring pattern 133a. The lower electrode input terminal 141 and the upper electrode input terminal 142 are connected to an external instrument that drives the actuator unit 130. Consequently, the actuator unit 130 is driven by drive voltage applied between the lower electrode input terminal 141 and the upper electrode input terminal 142 via the external instrument.

<Construction of Dispensing Apparatus>

Figure 6A:
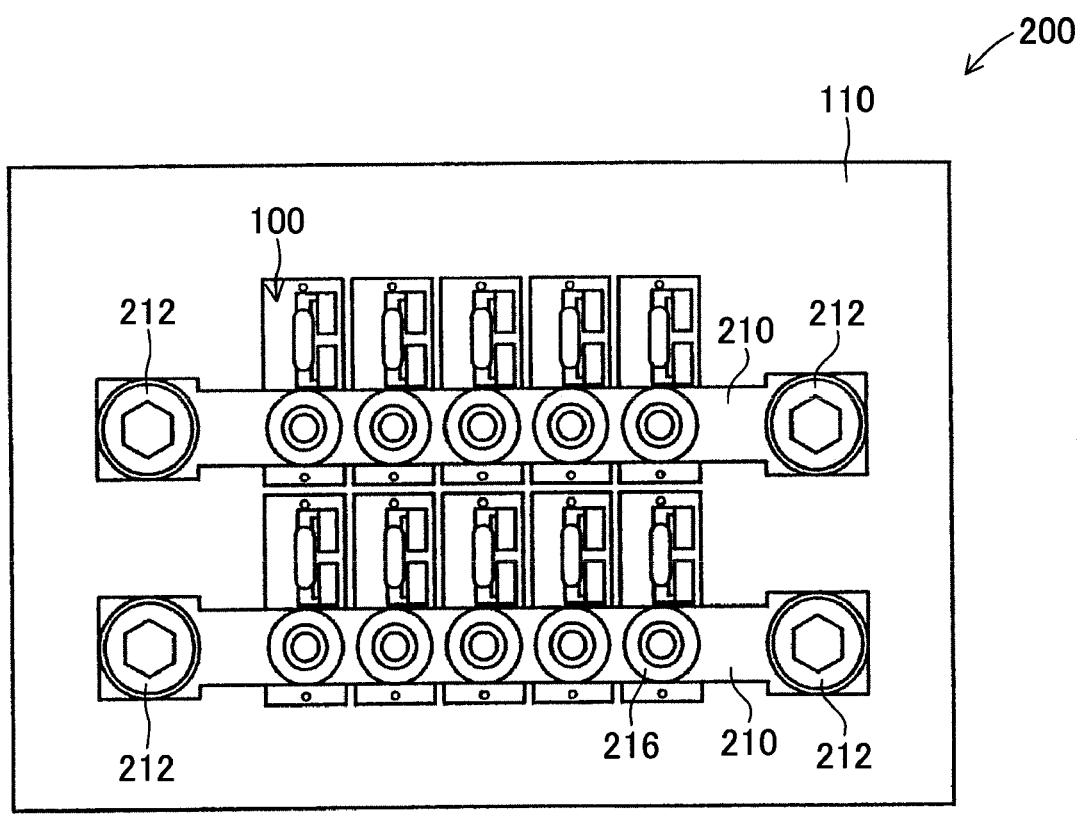
FIG. 6A is a plan view of a dispensing apparatus having the micropipette shown in FIG. 3.
Figure 6B:
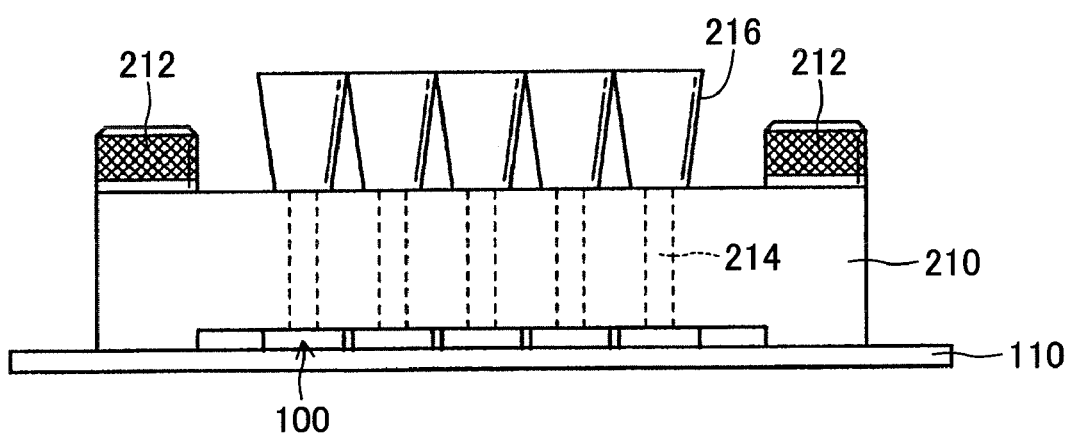
FIG. 6B is a side view of the dispensing apparatus having the micropipette shown in FIG. 3.
Figure 7:
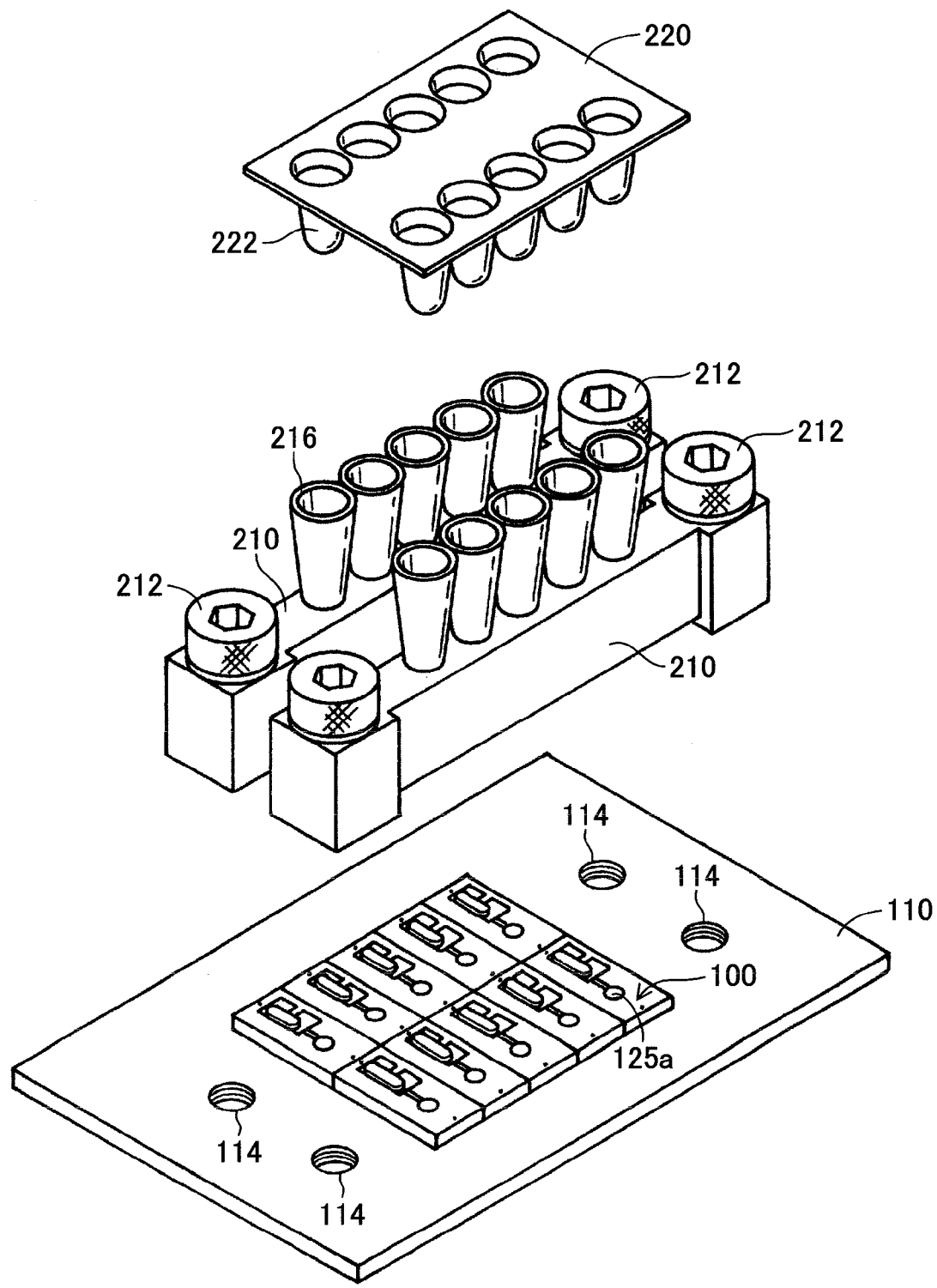
FIG. 7 is an exploded perspective view of the dispensing apparatus shown in FIGS. 6A and 6B.

Next, a dispensing apparatus 200 having the micropipette 100 with the above-stated construction will be described in detail. FIGS. 6A and 6B illustrate the construction of the dispensing apparatus 200 provided with the micropipette 100 shown in FIG. 5. Specifically, FIG. 6A is a plan view of the dispensing apparatus 200, and FIG. 6B is a side view of the dispensing apparatus 200. FIG. 7 is an exploded perspective view of the dispensing apparatus 200.

As shown in FIG. 6A, the dispensing apparatus 200 includes a plurality (10 in the drawing) of micropipettes 100 arranged in two dimensions. All the micropipettes 100 have a common nozzle plate 110, the construction of which has already been described above. The common nozzle plate 110 is a ceramic plate.

The dispensing apparatus 200 includes sample introduction members 210 for introducing the sample solution to the respective sample injection ports 125a of the micropipettes 110 (see FIG. 5). As shown in FIGS. 6A and 6B, the sample introduction members 210 are connected to the upper surfaces of the micropipettes 110 arranged in the two dimensions. As shown in FIG. 7, the sample introduction members 210 are fixed to the upper surface of the nozzle plate 110 by means of threaded holes 114 formed in the nozzle plate 110 and fixing bolts 212.

Referring to FIG. 6B, sample injection channels 214, which are constructed in the shape of a through-hole, are formed in each sample introduction member 210. The openings at the lower ends of the sample injection channels 214 are connected to the corresponding sample injection ports 125a of the micropipettes 110 (see FIG. 5). Also, the openings at the upper ends of the sample injection channels 214 are connected to the lower ends of introduction tubes 216, which are constructed in the shape of a trumpet whose diameter gradually increases upward.

Referring to FIG. 7, the plural introduction tubes 216 arranged in two dimensions are disposed and constructed such that the introduction tubes 216 are coupled with plural sample storage portions 222, which are formed at a cartridge 220 that stores a sample solution, while the sample storage portions 222 protrude downward from the cartridge 220. The cartridge 220 is formed by injection molding of a soft synthetic resin. The cartridge 220 is constructed such that openings are formed at the bottoms of the sample storage portions 222 using a needle, and therefore, the sample solution stored in the sample storage portions 222 is introduced into the introduction tubes 216, whereby different kinds of sample solutions are supplied to the respective sample injection ports 125a.

<General Construction of Passage Detection Apparatus According to a Preferred Embodiment>

Figure 8:
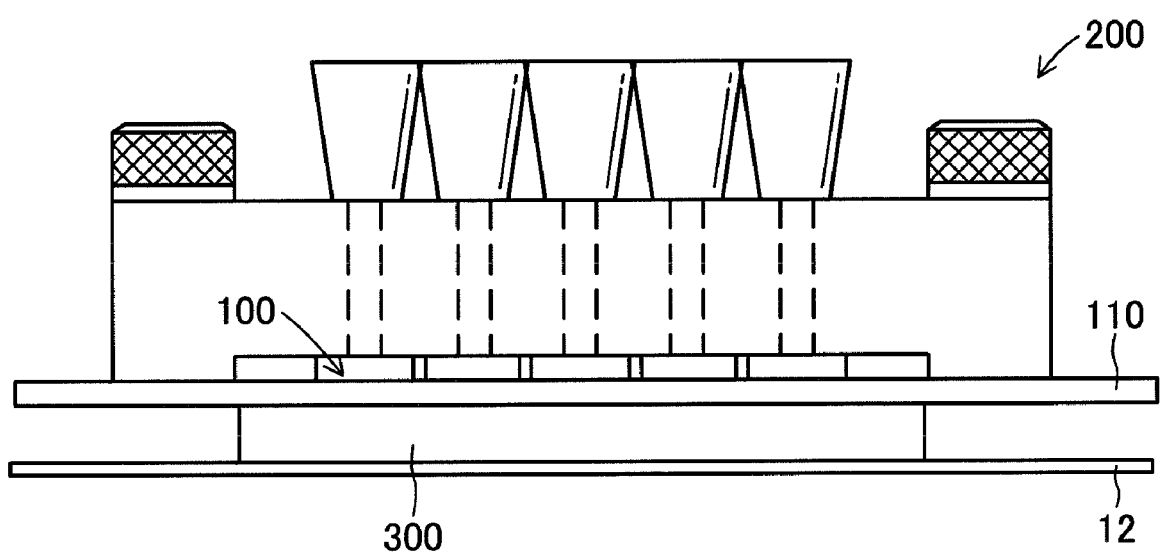
FIG. 8 is a side view illustrating a passage detection apparatus according to a preferred embodiment of the present invention, which is mounted in the dispensing apparatus shown in FIG. 6.
Figure 9:
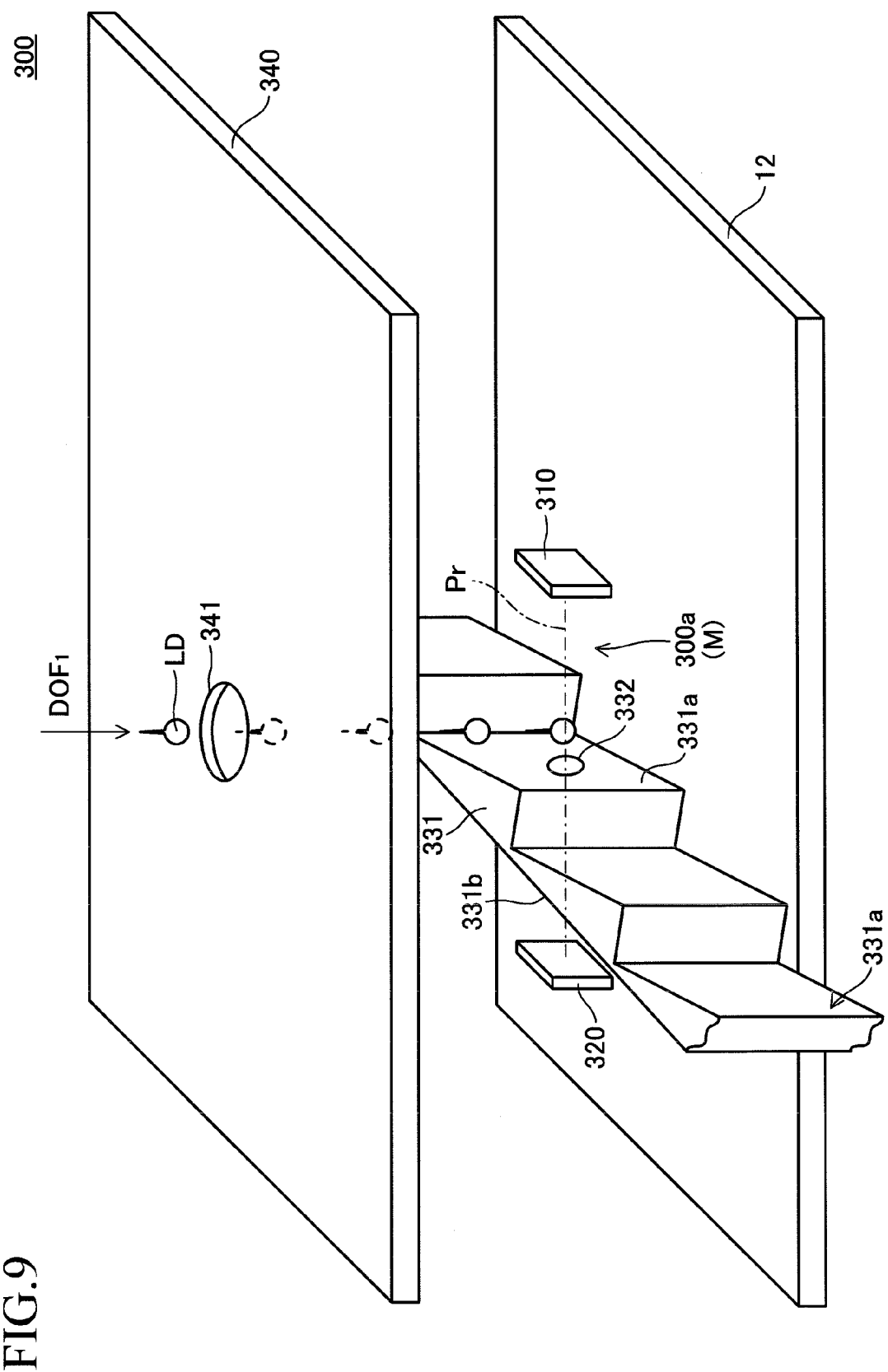
FIG. 9 is an enlarged perspective view of the passage detection apparatus shown in FIG. 8.
Figure 10:
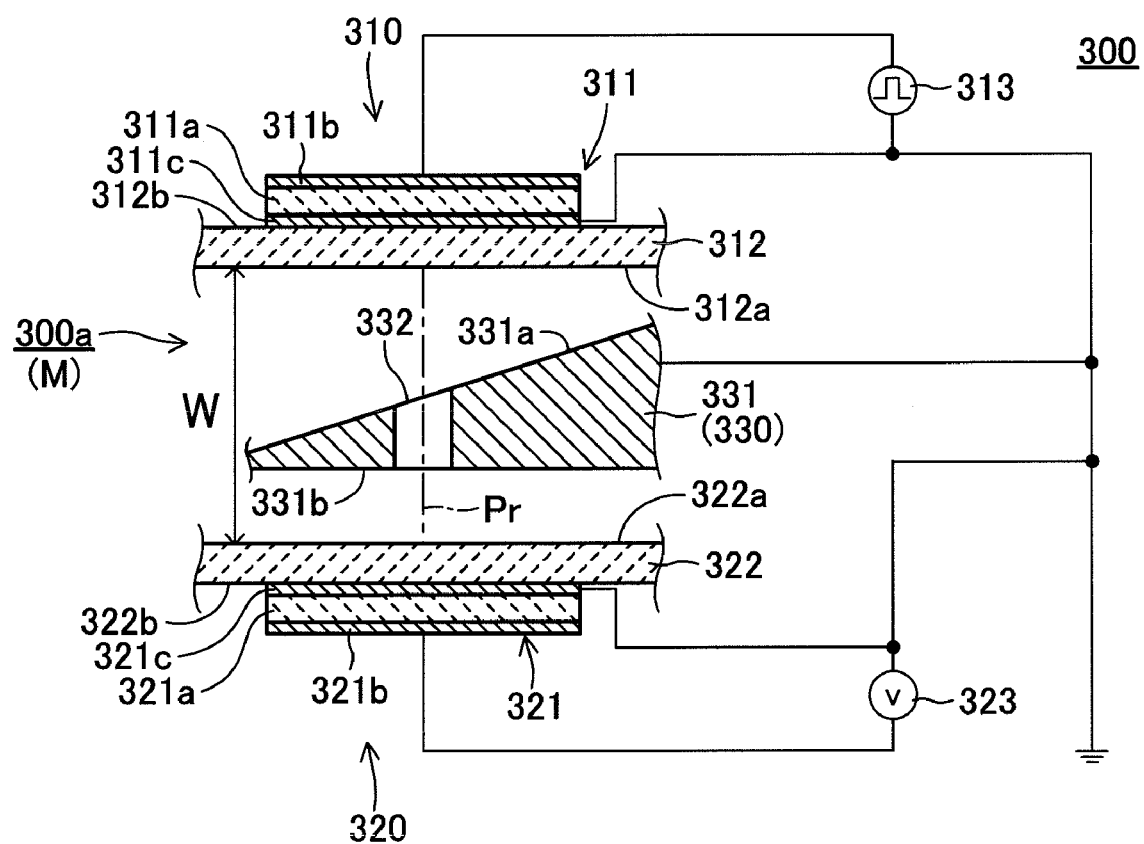
FIG. 10 is a sectional view of the passage detection apparatus shown in FIG. 9.

Next, the general construction of a passage detection apparatus according to a preferred embodiment of the present invention will be described in detail. FIG. 8 is a side view illustrating a passage detection apparatus 300 mounted between the nozzle plate 110, having sample solution ejection ports, of the dispensing apparatus 200 shown in FIG. 7 and the DNA chip substrate 12 constituting the DNA chip shown in FIG. 1. FIG. 9 is an enlarged perspective view of the passage detection apparatus 300 shown in FIG. 8 according to the present embodiment. FIG. 10 is a sectional view of the passage detection apparatus 300 shown in FIG. 9 according to the present embodiment.

Referring to FIG. 8, the passage detection apparatus 300 is configured as described below so as to be capable of detecting whether or not the sample solution is ejected to the DNA chip substrate 12 from each micropipette 100 at the dispensing apparatus 200.

Referring to FIG. 9, a transmitting device 310 and a receiving device 320 are provided so as to face each other across a specific space 300a. The specific space 300a is a space at the inside of the passage detecting apparatus 300, through which a micro drop LD of the sample solution passes.

<<Configuration of Transmitting Device>>

Referring to FIG. 10, the transmitting device 310 has a first piezoelectric/electrostrictive element 311. The first piezoelectric/electrostrictive element 311 is composed of a first piezoelectric/electrostrictive layer 311a, a drive electrode 311b, and a first reference electrode 311c.

The first piezoelectric/electrostrictive layer 311a is made of a thin plate of a piezoelectric/electrostrictive material (PZT or the like), for example. The drive electrode 311b and the first reference electrode 311c are constructed from a metallic film formed on both surfaces of the first piezoelectric/electrostrictive layer 311a.

The first piezoelectric/electrostrictive element 311 is supported on a first substrate 312 that is a thin ceramic plate. The first piezoelectric/electrostrictive element 311 is fixed to the outer surface 312b, which is reverse to the inner surface 312a facing the specific space 300a, of the first substrate 312. Specifically, the first piezoelectric/electrostrictive element 311 is formed so as to be integral with the first substrate 312 by forming a coating layer, which is a base of the first piezoelectric/electrostrictive layer 311a, drive electrode 311b and first reference electrode 311c, and sintering the resultant.

An output terminal of a high voltage of a pulse generating source 313 that generates a pulse signal is connected to the drive electrode 311b of the first piezoelectric/electrostrictive element 311. The first reference electrode 311c is grounded. The first reference electrode 311c is provided at the side of the first substrate 312 (at the side of the specific space 300a).

Thus, the first piezoelectric/electrostrictive element 311 is configured to produce a vibration by applying a voltage in the form of a pulse between the drive electrode 311b and the first reference electrode 311c from the pulse generating source 313. The transmitting device 310 is configured to propagate supersonic wave to a medium (such as an air, etc.) in the specific space 300a through the vibration of the first piezoelectric/electrostrictive element 311.

<<Configuration of Receiving Device>>

Referring to FIGS. 9 and 10, the receiving device 320 is arranged so as to face the transmitting device 310 across the specific space 300a. The receiving device 320 produces an output corresponding to the vibration that is transmitted from the transmitting device 310 to propagate through the medium M in the specific space 300a.

Specifically, referring to FIG. 10, the receiving device 320 includes a second piezoelectric/electrostrictive element 321. The second piezoelectric/electrostrictive element 321 is composed of a second piezoelectric/electrostrictive layer 321a, a signal output electrode 321b, and a second reference electrode 321c. This second piezoelectric/electrostrictive element 321 also has the structure same as that of the first piezoelectric/electrostrictive element 311.

Specifically, the second piezoelectric/electrostrictive element 321 is supported on a second substrate that is a thin ceramic plate. The second piezoelectric/electrostrictive element 321 is fixed on the outer surface 322b, which is reverse to the inner surface 322a facing the specific space 300a, of the second substrate 322.

The second piezoelectric/electrostrictive element 321 is configured to produce a voltage between the signal output electrode 321b and the second reference electrode 321c, according to a stress produced on the second piezoelectric/electrostrictive layer 321a by the vibration of the second substrate 322.

A voltmeter 323 is connected to the second piezoelectric/electrostrictive element 321 for acquiring a voltage between the signal output electrode 321b and the second reference electrode 321c. The grounded second reference electrode 321c is provided at the side of the second substrate 322 (at the side of the specific space 300a).

Specifically, the second piezoelectric/electrostrictive element 321 is configured such that a voltage is produced at both ends of the voltmeter 323 according to the stress applied to the second piezoelectric/electrostrictive element 321 by the vibration of the second substrate 322 that is caused by the propagation of supersonic wave to the second substrate 322 through the medium M (e.g., air) in the specific space 300a.

Thus, the passage detection apparatus 300 according to the present embodiment determines whether or not the micro drop LD (see FIG. 9) of the sample solution passes through the specific space 300a or determines the volume of the micro drop LD through the detection of the change in the propagation state of the supersonic wave in the specific space 300a based upon the change in the voltage at both ends of the voltmeter 323.

<<Arrangement of Transmitting Device and Receiving Device>>

Referring to FIG. 10, the first piezoelectric/electrostrictive element 311 and the second piezoelectric/electrostrictive element 321 are arranged so as to form the specific space 300a between the first reference electrode 311c and the second reference electrode 321c in the present embodiment. Specifically, the first piezoelectric/electrostrictive element 311 is arranged such that the first reference electrode 311c is closer to the specific space 300a than the drive electrode 311b. The second piezoelectric/electrostrictive element 321 is arranged such that the second reference electrode 321c is closer to the specific space 300a than the signal output electrode 321b.

Thus, in the passage detection apparatus 300 according to the present embodiment, the specific space 300a is arranged so as to be sandwiched between the grounded first reference electrode 311c and the grounded second reference electrode 321c. Specifically, since the generation of an electric field in the specific space 300a is suppressed, the passage detection apparatus 300 of the present embodiment prevents that the flight route of the micro drop LD is curved by the electric field in case where the micro drop LD of the sample solution (see FIG. 9) is charged.

The width W of the specific space 300a is set to meet the following equation when the wavelength of the vibration transmitting through the medium M (air, etc.) in the specific space 300a is defined as λ and n is defined as a natural number.

$$W=(n/2)\lambda$$

In the present embodiment, the first piezoelectric/electrostrictive element 311 is provided at the outer surface of the first substrate 312. The second piezoelectric/electrostrictive element 321 is provided at the outer surface 322b of the second substrate 322. Specifically, the first piezoelectric/electrostrictive element 311 and the second piezoelectric/electrostrictive element 321 are arranged at the outside of the specific space 300a (so as not to be exposed to the inside of the specific space 300a).

<<Configuration of Shielding Member>>

Referring to FIGS. 9 and 10, a shielding member 330 is arranged between the transmitting device 310 and the receiving device 320. The shielding member 330 is made of a conductive metallic plate member.

Referring to FIG. 10, the shielding member 330 is electrically connected to the second reference electrode 321c so as to have the potential same as the potential of the second reference electrode 321 of the receiving device 320. Further, the shielding member 330 is grounded. Specifically, the shielding member 330 is configured to function as a shielding plate for electromagnetically shielding the receiving device 320.

Referring to FIGS. 9 and 10, the shielding member 330 has a shielding plate 331 made of a plate-like member. The shielding plate 331 is formed into a wedge-like shape viewed from the direction that is parallel to the predetermined flight direction $DOF_1$ and is along the route through which the micro drop LD of the sample solution passes.

A first opposite face 331a of the shielding plate 331, which is one surface in the direction along a direct vibration propagating route Pr, is provided to face the transmitting device 310. On the other hand, a second opposite face 331b, which is the other surface in the aforesaid direction, is provided to face the receiving device 320. The direct vibration propagating route Pr is a straight line linking the center of the transmitting device 310 and the center of the receiving device 320.

In the present embodiment, the first opposite face 331a is provided as an inclined surface. Specifically, the shielding plate 331 is arranged such that the normal of the first opposite face 331a crosses the direct vibration propagating route Pr.

The second opposite face 331b is provided so as to be generally orthogonal to the direct vibration propagating route Pr.

A through-hole 332 is formed to the shielding plate 331. The through-hole 332 is formed so as to face the route through which the micro drop LD of the sample solution passes. The through-hole 332 is formed on the direct vibration propagating route Pr that is generally orthogonal to the route through which the micro drop LD of the sample solution passes.

In the present embodiment, the shielding member 330 is configured to meet the inequalities of:

$$d2^2/d1^2 \geq 0.6, (d1-d2)/v \geq 3T$$

wherein the circle-equivalent diameter of the through-hole 332 is defined as d1, the circle-equivalent diameter of the micro drop LD of the sample solution is defined as d2, the average speed of the micro drop LD of the sample solution at the through-hole 332 is defined as v, and the cycle of the vibration generated from the transmitting device 310 is defined as T.

It is to be noted that the circle-equivalent diameter of the through-hole 332 means the diameter of the circle having an area same as the area of the through-hole 332 on a plane (in the present embodiment, the second opposite face 331b) having a straight line parallel to the direct vibration propagating route Pr serving as the normal, when the through-hole 332 is projected on the plane. The same is true for the circle-equivalent diameter of the micro drop LD of the sample solution.

In the present embodiment, the through-hole 332 is formed into generally a cylindrical shape in which the direct vibration propagating route Pr is defined as a central axis. Specifically, the through-hole 332 is formed into generally a cylindrical shape viewed from the direction along the direct vibration propagating route Pr.

<<Configuration of Aperture Plate>>

A flat-plate aperture plate 340 is arranged so as to face the DNA chip substrate 12 across the transmitting device 310, receiving device 320, and shielding member 330. The aperture plate 340 is arranged at an inlet-side end portion for the micro drop LD of the specific space 300a so as to cross the passing direction of the micro drop LD of the sample solution.

A drop passing aperture 341, which is a through-hole through which the micro drop LD of the sample solution can pass, is formed to the aperture plate 340. The drop passing aperture 341 is formed to have a size sufficiently smaller than the width of the specific space 300a. Specifically, the drop passing aperture 341 is formed to have a size sufficiently smaller than the size of the specific space 300a in the section vertical to the passing direction of the micro drop LD of the sample solution.

In the present embodiment, the transmitting device 310, receiving device 320, shielding member 330, and aperture plate 340 are configured and arranged in such a manner that, when the flight direction of the micro drop LD of the sample solution coincides with the predetermined flight direction $DOF_1$, the micro drop LD passes the center of the drop passing aperture 341 and the direct vibration propagating route Pr.

<Circuit Construction for Determination of Passage of Object>

Figure 11:
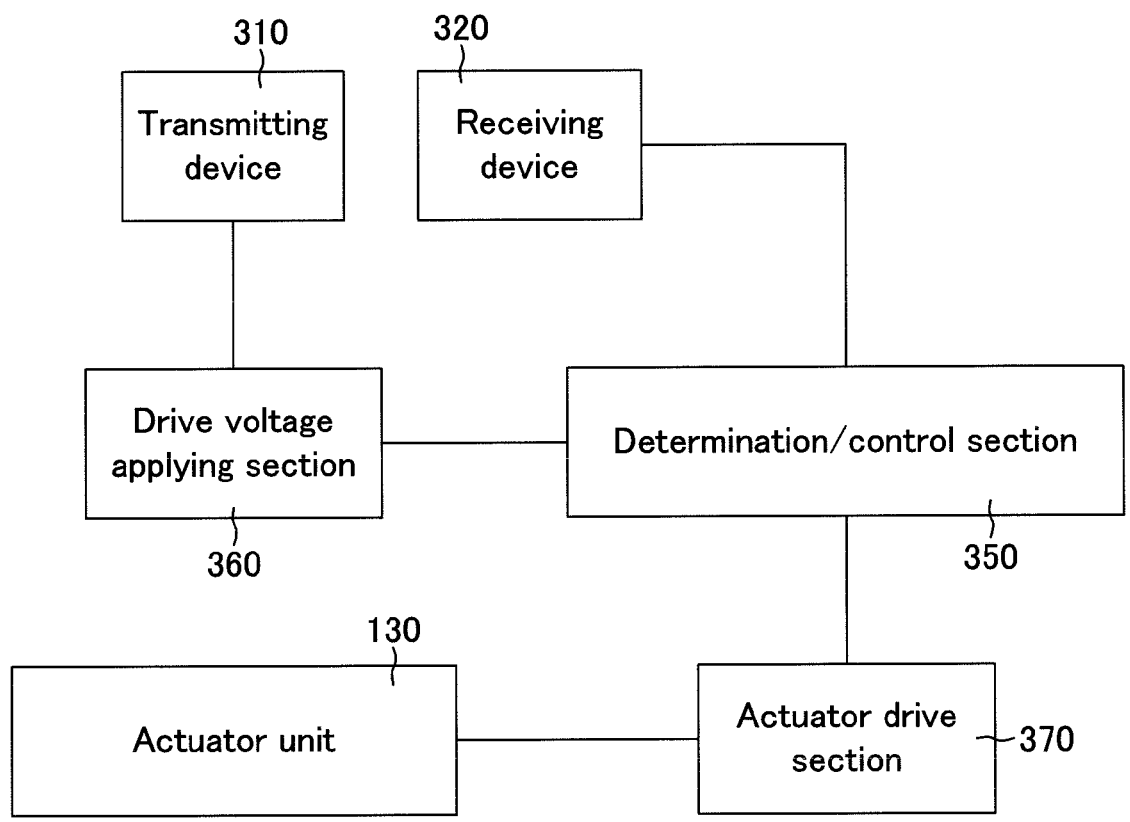
FIG. 11 is a block diagram schematically showing a construction of an electric circuit applied to the passage detection apparatus shown in FIG. 10.

FIG. 11 is a block diagram schematically showing a construction of an electric circuit applied to the passage detecting apparatus shown in FIG. 10. Hereafter, the circuit construction for determining the ejecting state of the micro drop of the sample solution from the micropipette chip 100 shown in FIG. 8 will be explained with the use of FIG. 11.

A determination/control section 350 includes a CPU, etc. for controlling the overall operation of the present apparatus. The determination/control section 350 is connected to the receiving device 320, drive voltage applying section 360, and actuator drive section 370.

The drive voltage applying section 360 includes the pulse generating source 313 for applying a drive voltage to the transmitting device 310 (the first piezoelectric/electrostrictive element 311 in FIG. 10). The determination/control section 350 controls the drive voltage applying section 360, thereby applying a drive voltage having an arbitrary waveform to the transmitting device 310.

The determination/control section 350 is connected to the receiving device 320 (the second piezoelectric/electrostrictive element 321 in FIG. 10) for receiving an output signal from the receiving device 320. Specifically, the determination/control section 350 is configured to include the voltmeter 323 in FIG. 10. The determination/control section 350 receives an output generated from the receiving device 320 and determines the ejecting state of the micro drop of the sample solution on the basis of the output.

The actuator drive section 370 is connected to the lower electrode input terminal 141 and the upper electrode input terminal (see FIG. 5) in the actuator unit 130. The determination/control section 350 is configured to control the drive (i.e., the ejection of the micro drop of the sample solution) of the actuator unit 130 through the actuator drive section 370.

<Description of Operation of Apparatus According to Embodiment>

Next, the operation of the apparatus with the above-mentioned construction according to the embodiment will be described with reference to the drawings.

<<Manufacturing Process of DNA Chip>>

First, the manufacturing process of the DNA chip 10 shown in FIG. 1 will be described. The manufacturing process includes a pre-treatment process of forming a sample support layer 14 (see FIG. 2), which is a poly-L-lysine layer, on the surface of the DNA chip substrate 12, a sample manufacturing process of manufacturing a sample solution containing DNA pieces, and a supply process of supplying the manufactured sample solution onto the DNA chip substrate 12.

The pre-treatment process is carried out as follows. First, the DNA chip substrate 12 is soaked in a predetermined alkali solution at the room temperature for at least two hours. As the alkali solution, for example, there may be used a solution obtained by dissolving NaOH in distilled water, adding ethanol in the mixture, and stirring the mixture until the mixture becomes fully transparent. After that, the DNA chip substrate 12 is taken out of the alkali solution, and is then washed in distilled water. Subsequently, the DNA chip substrate 12 is soaked in a poly-L-lysine solution manufactured by adding poly-L-lysine in distilled water for approximately one hour. After that, the DNA chip substrate 12 is taken out of the poly-L-lysine solution, and the poly-L-lysine solution remaining on the DNA chip substrate 12 is removed by centrifugal separation. Subsequently, the DNA chip substrate 12 is dried at 40° C. for approximately 5 minutes. In this way, a DNA chip substrate 12 having the poly-L-lysine sample support layer 14 formed on the surface thereof is obtained.

The sample manufacturing process includes an amplifying process of amplifying the base sequence of the DNA pieces, using polymerase chain reaction (PCR), to obtain a PCR product, a powder producing process of drying the obtained PCR product to obtain DNA powder, and a mixing process of dissolving the obtained DNA powder in a buffer solution. In the powder producing process, first, sodium acetate of 3M (=3 mol/l) and isoprophanol are added to the PCR product, and the mixture is left for a few hours. After that, the solution is centrifugally separated, and therefore, the DNA pieces are precipitated. The precipitated DNA pieces are rinsed using ethanol, are centrifugally separated, and are then dried. As a result, DNA powder is produced. In the mixing process, a Tris-EDTA (TE) buffer solution is added to the DNA powder, and the mixture is left for a few hours until the DNA powder is fully dissolved in the buffer solution. As a result, a sample solution is prepared. The concentration of the sample solution prepared at this step is 1 to 10 µg/µl The sample solution obtained as described above is stored in the sample storage portions 222 of the cartridge 220 shown in FIG. 7. Since the cartridge 220 is mounted to the dispensing apparatus 200 shown in FIG. 6, the sample solution is supplied into the respective micropipettes 100 in the dispensing apparatus 200. And the micro drops of the sample solution are ejected toward the DNA chip substrate 12 (see FIG. 1) from the respective micropipettes 100, and therefore, the micro drops of the sample solution are supplied onto the DNA chip substrate 12. As a result, plural micro spots S of the sample solution are formed on the DNA chip substrate 12 in a predetermined array. In this way, the DNA chip 10 is manufactured.

Here, it is difficult to observe the micro drops of the sample solution with the naked eye. For this reason, the determination as to whether or not the micro drops of the sample solution are properly formed on the DNA chip substrate 12 in the predetermined array (whether the ejecting operation is not correctly carried out, for example, the micro drops are not ejected, in one or more specific micropipettes 110) cannot be performed with the naked eye. On the other hand, it is possible to determine whether the micro drops are not ejected by scanning the ejection route of the micro drops with a laser beam. However, the construction of an apparatus for determining whether the ejecting operation is not correctly carried out in the respective micropipettes 100 by scanning with a laser beam as described above is very expensive.

On the contrary, the determination as to whether the ejecting operation is not correctly carried out in the respective micropipettes 100 of the dispensing apparatus 200 is accomplished using the passage detection apparatus 300 according to the preferred embodiment of the present invention as shown in FIG. 8. As described above, the construction of the passage detection apparatus 300 is very simple, and therefore, the manufacturing costs of the passage detection apparatus 300 are very low. Although the construction of the passage detection apparatus 300 is very simple as described above, it is possible for the passage detection apparatus 300 to accurately perform the determination as to whether the ejecting operation is not correctly carried out.

<<Description of Object Passage Determination Operation According Embodiment>

Next, the determining operation of the ejection state of the micro drops of the sample solution in the micropipettes 100 using the passage detection apparatus 300 according to this embodiment will be described in detail with reference to the drawings.

As shown in FIG. 8, the passage detection apparatus 300 is disposed below the nozzle plate 110 of the micropipettes 100. Specifically, the passage detection apparatus 300 is arranged at the lower part of the dispensing apparatus 200 such that the nozzle plate 110 faces the aperture plate 340 (see FIG. 9) of the passage detection apparatus 300. The dispensing apparatus 200 is driven by an external device. Specifically, the actuator unit 130 (see FIG. 5) of each micropipette 100 mounted to the dispensing apparatus 200 is driven. Accordingly, micro drops of the sample solution are ejected from the respective micropipettes 100.

Here, the passage detection apparatus 300 is arranged in such a manner that the nozzle 112 (see FIG. 3) and the drop passing aperture 341 (see FIG. 9) are arranged on a straight line parallel to the predetermined flight direction $DOF_1$ (see FIG. 9). By virtue of this configuration, when the ejecting direction is not appropriate (the ejecting direction is not parallel to the predetermined flight direction $DOF_1$ shown in FIG. 9) even if the micro drops LD (see FIG. 9) of the sample solution are ejected from the micropipettes 100, the micro drops LD collide with the aperture plate 340 so as not to pass through the drop passing aperture 341.

Referring to FIG. 9, when the micro drops LD of the sample solution are ejected parallel to the predetermined flight direction DOF1, the micro drops LD pass the drop passing aperture 341. The micro drops LD passing through the drop passing aperture 341 enter the specific space 300*a*. Accordingly, the state (propagation state of supersonic wave, dielectric constant, etc.) of the inside of the specific space 300*a* changes. The degree of the change is different depending upon the property of the micro drops LD. Thus, the state of the inside of the specific space 300*a* is detected by the receiving device 320, whereby the passage state of the micro drops LD in the specific space 300*a* can be detected. Specifically, whether the micro drops LD enter the specific space 300*a* or not, and the size of the micro drops LD are determined.

<<<Description of Operation of Object Passage Determination>>>

Referring to FIGS. 10 and 11, the determination/control section 350 controls the drives of the actuator unit 130 and the transmitting device 310 (first piezoelectric/electrostrictive element 311) in such a manner that the drive of the transmitting device 310 (first piezoelectric/electrostrictive element 311) is synchronous with the drive of the actuator unit 130. With this configuration, the first piezoelectric/electrostrictive element 311 and the first substrate 312 vibrate, whereby supersonic wave is generated. The supersonic wave propagates through the medium M in the specific space 300*a* to reach the second substrate 322. Thus, the second substrate 322 is vibrated. By the vibration of the second substrate 322, a voltage is generated on the receiving device 320 (second piezoelectric/electrostrictive element 321).

Figure 12:
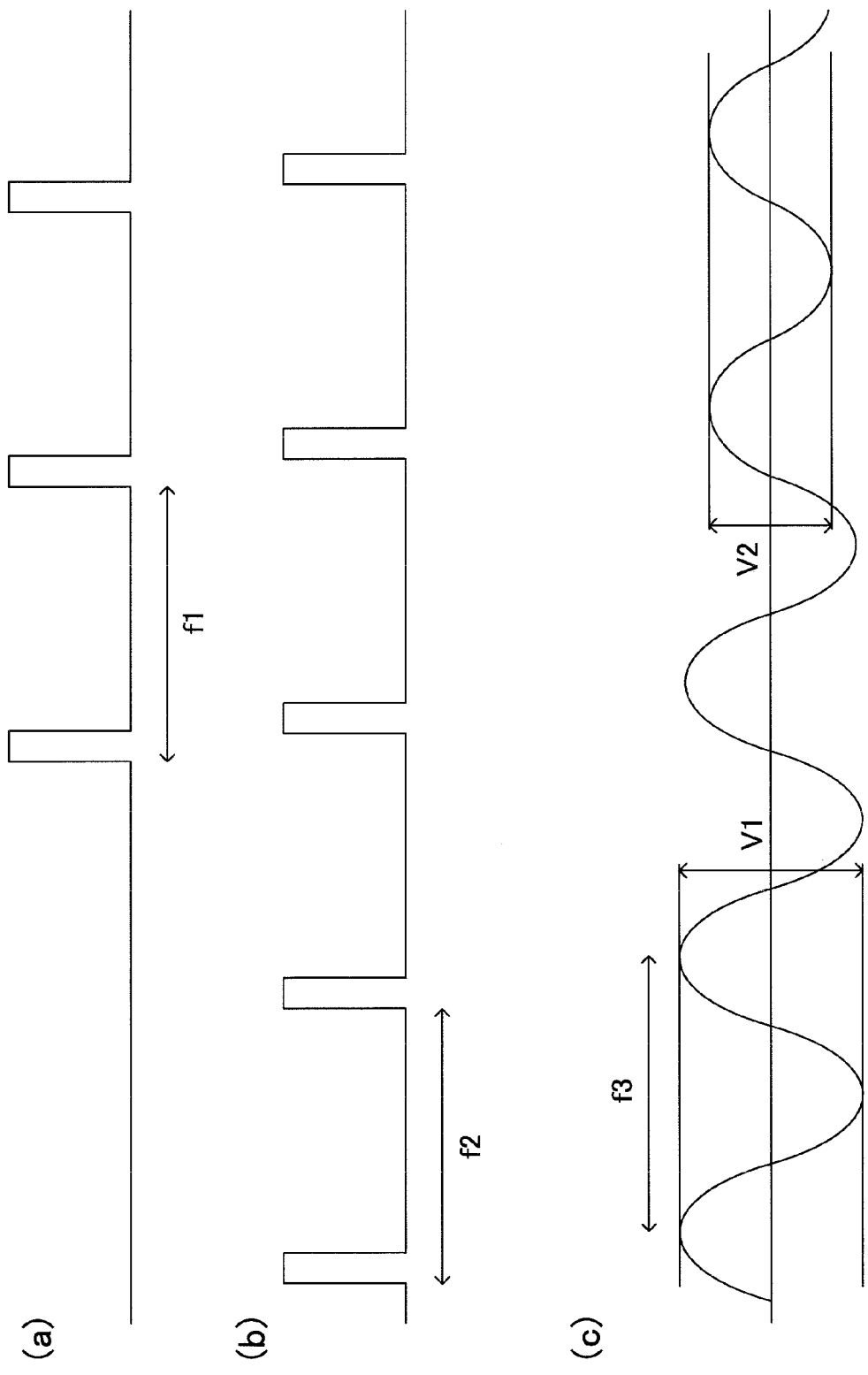
FIG. 12 is a signal chart showing the state of the drive control of the dispensing apparatus and the state of a detection of passage of an object at the determination/control section shown in FIG. 11.

Referring to FIG. 12, for example, the actuator unit 130 (see FIG. 11) is periodically driven by a pulse wave having a predetermined cycle (frequency f1) as illustrated in a time chart (a). The drive pulse of the actuator unit 130 is generated synchronous with the pulse wave having the predetermined cycle (frequency f2) for driving the transmitting device 310 (first piezoelectric/electrostrictive element 311 in FIG. 10) as illustrated in a time chart (b). In this case, the frequency f1 is generally equal to the frequency f2. Further, the frequency f2 is a resonant frequency of the transmitting device 320 (first piezoelectric/electrostrictive element 311 in FIG. 10). Accordingly, a waveform illustrated in a time chart (c) is generated on the receiving device 320 (second piezoelectric/electrostrictive element 321 in FIG. 10). This waveform is generated with a predetermined cycle (frequency f3). In this case, the frequency f3 is generally equal to the frequency f1 and f2.

The vibration state of the second substrate 322 changes according to the propagating state of the vibration in the specific space 300*a*. The propagating state of the vibration in the specific space 300*a* differs depending upon the presence of the micro drops in the specific space 300a or the size of the micro drops. Therefore, whether the micro drops enter the specific space 300a or not and the size of the micro drops are determined, through the detection of the change in the propagating state in the specific space 300a by the receiving device 320.

Referring to FIG. 12, a voltage Vpp (peak-to-peak voltage) is V1 at the output waveform (see the time chart (c)) of the receiving device 320 before the actuator unit 130 (see FIG. 11) is driven. On the other hand, the voltage Vpp (peak-to-peak voltage) becomes V2, which is smaller than V1, at the output waveform (see the time chart (c)) of the receiving device 320 after the actuator unit 130 (see FIG. 11) is driven and when the micro drops enter the specific space 300a (see FIG. 10). Thus, the output voltage of the receiving device 320 is acquired, whereby whether the micro drops enter the specific space 300a or not and the size of the micro drops are determined.

<Operation and Effect of Construction of Apparatus According to Embodiment>

Next, the operation and effect according to the construction of the apparatus of the present embodiment will be described with reference to the drawings.

Referring to FIGS. 9 and 10, the passage detection apparatus 300 in the present embodiment is formed with a direct propagation route of a vibration (direct vibration propagating route Pr) that reaches the receiving device 320 from the transmitting device 310 through the through-hole 332 of the shielding member 330 and the passage route of the micro drop LD of the sample solution. On the other hand, the reception of the vibration, which is multiply reflected in the specific space 300a, by the receiving device 320 is suppressed by the shielding member 330. Specifically, the receiving device 320 can be shielded from the multiply reflected vibration by the shielding member 330.

By virtue of this configuration, the S/N ratio in the detection of the passage of the micro drop LD of the sample solution is enhanced. Accordingly, the passage detection of the micro drop LD having a more micro size can be carried out more correctly.

The passage detection apparatus 300 according to the present embodiment is formed with the first opposite face 331a, which is an inclined face in which the direction crossing the direct vibration propagating route Pr (direct vibration propagating direction) is defined as the normal, by the shielding plate 331 of the shielding member 330. The vibration multiply reflected in the specific space 300a can be reflected in the direction greatly deviated from the direct vibration propagating route Pr, which links the through-hole 332 and the receiving device 320, by the first opposite face 331a.

Thus, the reception of the vibration, caused by the multiple reflection, by the receiving device 320 can more effectively be suppressed. Accordingly, the S/N ratio in the detection of the passage of the micro drop LD of the sample solution is more enhanced.

In the passage detection apparatus 300 according to the present embodiment, the inequalities of $d2^2/d1^2 \geqq 0.6$, $(d1-d2)/v \geqq 3T$ are satisfied wherein the circle-equivalent diameter of the through-hole 332 is defined as d1, the circle-equivalent diameter of the micro drop LD of the sample solution is defined as d2, the average speed of the micro drop LD of the sample solution at the through-hole 332 is defined as v, and the cycle of the vibration generated from the transmitting device 310 is defined as T.

Accordingly, when the vibration generated from the transmitting device 310 passes through the through-hole 332, the state in which the through-hole 332 is overlapped with the micro drop LD of the sample solution continues for the period sufficient for the passage detection of the micro drop LD of the sample solution. Therefore, the rate of change of the output signal from the receiving device 320 by the passage of the micro drop LD can be produced by the amount sufficient for the passage detection of the micro drop LD. Consequently, the passage detection of the micro drop LD is more stably carried out.

In the passage detection apparatus 300 according to the present embodiment, the shielding member 330 is set to have a ground potential same as the potential of the second reference electrode 321c of the receiving device 320.

By virtue of this configuration, the shielding member 330 provides not only the shield effect to the multiply reflected vibration but also the shield effect to electromagnetic noise. Therefore, the S/N ratio in the detection of the passage of the micro drop LD of the sample solution is more enhanced. Accordingly, the detection of the micro drop LD, having a more micro size, of the sample solution can more correctly be performed.

In the passage detection apparatus 300 according to the present embodiment, the aperture plate 340 is formed with the drop passing aperture 341 that is a through-hole through which the micro drop LD of the sample solution can pass.

Accordingly, the flight state (e.g., advancing direction or linearity, etc.) of the micro drop LD of the sample solution in the specific space 300a can be detected with a simple construction by appropriately setting the positional relationship between the specific space 300a and the drop passing aperture 341.

In the passage detection apparatus 300 according to the present embodiment, the specific space 300a is sandwiched between the grounded first reference electrode 311c and the grounded second reference electrode 321c. Therefore, when the micro drop of the sample solution is charged, it is prevented that the flight route of the micro drop is curved by the electric field, whereby the ejecting state can surely be detected.

In the passage detection apparatus 300 according to the present embodiment, the width W of the specific space 300a is set to meet the following equation:

$$W=(n/2)\lambda$$

wherein the wavelength of the vibration propagating through the medium M in the specific space 300a is defined as $\lambda$ and n is defined as a natural number.

Accordingly, the propagation of the vibration in the specific space 300a is efficiently performed. Consequently, power saving of the first piezoelectric/electrostrictive element 311 constituting the vibration generating source is possible. Further, the sensitivity of the second piezoelectric/electrostrictive element 321 can be enhanced.

In the passage detection apparatus 300 according to the present embodiment, the first piezoelectric/electrostrictive element 311 and the second piezoelectric/electrostrictive element 321 are arranged at the outside of the specific space 300a (so as not to be exposed to the inside of the specific space 300a). Specifically, the inner wall surface of the specific space 300a is composed of the surface of the dielectric member. Accordingly, it can be prevented that a defect is caused on the first piezoelectric/electrostrictive element 311 and the second piezoelectric/electrostrictive element 321 caused by the adhesion of the sample solution to the first piezoelectric/electrostrictive element 311 and the second piezoelectric/electrostrictive element 321.

<Suggestion of Modifications>

The above-described embodiment has been disclosed merely to illustrate representative embodiment of the present invention considered as the most preferred embodiments at the time of the filing of the present application. Consequently, the present invention is not limited to the above-described embodiments, and it is appreciated that various modifications are possible without changing essential parts of the present invention.

Hereinafter, a few modifications will be illustrated within the limits of addition possible at the time of filing of the present application (as far as time is allowed) under the first-to-file rule. However, it is not necessary to mention that the present invention is also not limited to these modifications. Limiting the present invention based on the disclosures of the embodiments described above and the modifications described below (especially, limiting the respective components constituting the means to solve the problems of the present invention, particularly, the components which are expressed operatively and functionally, based on the description of the preferred embodiments) is not allowed because the limitation trespasses on benefits of the applicant who has hastened to file the application under the first-to-file rule, the limitation provides imitators with undue profits, and therefore, the limitation is opposed to the purpose of the patent law prescribing the protection and utilization of the invention. Furthermore, it is not necessary to mention that the following modifications can be appropriately combined with each other within the scope of consistency.

(i) The present invention is not limited to the micropipettes disclosed in the above-described embodiment. Also, the flight direction of the micro object is not limited to the vertically-downward direction. As the vibration used for the passage detection, sound wave or heat can be utilized in addition to supersonic wave. Further, there is no limitation on the medium through which the micro object passes. For example, the present invention is preferably applicable even in case where various gases in addition to air, or liquid such as water, oil, etc. are used as the medium.

(ii) Referring to FIG. 9, the shape of the through-hole 332 viewed from the direction along the direct vibration propagating route Pr is not limited to be circular. The through-hole 332 can be formed into various shapes, such as an ellipse, polygon, indeterminate form, etc. Further, from the viewpoint of the detection sensitivity, it is preferable that the shape of the through-hole 332 and the circle-equivalent diameter are set in accordance with the size of the micro drop LD of the sample solution in such a manner that the area in the event that the micro drop LD of the sample solution is projected on the plane (second opposite face 331b) having the straight line parallel to the direct vibration propagating route Pr defined as the normal becomes not less than 60% of the open area of the through-hole 332.

(iii) Referring to FIG. 9, the angle made by the first opposite face 331a and the direct vibration propagating route Pr may be set to 40 degrees to 55 degrees.

In the configuration described above, the vibration multiply reflected in the specific space 300a is reflected by the first opposite face 331a that is an inclined face formed by the shielding plate 331. By virtue of this configuration, the propagating direction of the reflected vibration may be greatly deviated from the direct vibration propagating route Pr linking the through-hole 332 and the receiving device 320. Accordingly, the reception of the vibration caused by the multiple reflection by the receiving device 320 can be more effectively suppressed.

According to this configuration, the S/N ratio in the detection of the passage of the micro drop LD of the sample solution is more enhanced. Therefore, the detection of the micro drop LD, having a more micro size, of the sample solution can be more correctly performed.

(iv) Referring to FIG. 9, the first opposite face 331a may be the face generally orthogonal to the direct vibration propagating route Pr, and the second opposite face 331b may be an inclined face. Alternatively, the first opposite face 331a and the second opposite face 331b may both be inclined faces.

(v) The shielding member 330 may be made of a semiconductive material or insulating material.

Figure 13:
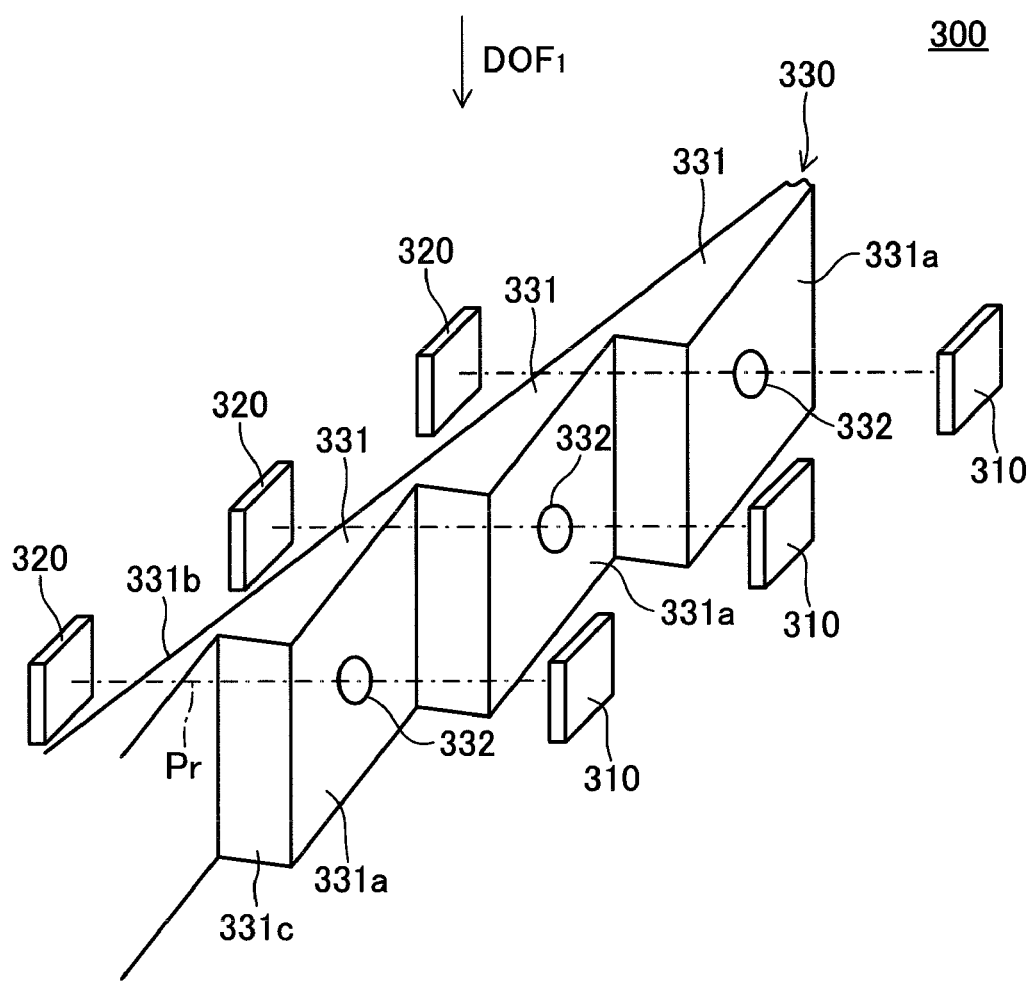
FIG. 13 is a perspective view showing one modification of the passage detection apparatus shown in FIG. 9.

(vi) FIG. 13 is a perspective view showing a configuration according to one modification of the passage detection apparatus 300 shown in FIG. 9. As shown in FIG. 13, plural sets of a pair of the transmitting device 310 and the receiving device 320 may be provided.

In this case, the transmitting devices 310 and the receiving devices 320 are arranged along the longitudinal direction of the shielding member 330 (in the direction orthogonal to the direct vibration propagating route Pr and the predetermined flight direction $DOF_1$: in the direction from the lower-left side toward the upper-right side in the figure). The shielding member 330 includes plural shielding plates 331 arranged along the longitudinal direction. Specifically, as shown in FIG. 13, the shielding plates 331, each having the through-hole 332 formed thereto, are arranged so as to correspond to each of the plural sets of the transmitting device 310 and the receiving device 320. These plural shielding plates 331 are seamlessly and integrally formed.

In this modification, the shielding member 330 is configured in such a manner that the second opposite faces 331b of the plural shielding plates 331 are positioned on the same plane. The shielding member 330 is also configured such that a connection face 331c, which is a flat face for connecting the adjacent first opposite faces 331a parallel to each other, and the first opposite face 331a are generally orthogonal to each other.

As described above, the shielding member 330 in this modification is formed into a serrated shape in which the wedge-like shielding plates 331 are joined.

According to this configuration, the occurrence of crosstalk between the adjacent receiving devices 320 can effectively be prevented by the shielding plate 331 facing each receiving device 320. Therefore, the passage of the object having a more micro size can be more correctly detected.

(vii) As shown in FIG. 13, the aperture plate 340 (see FIG. 9) may be appropriately omitted.

(viii) The shape of the shielding member 330 is not limited to the shapes shown in FIGS. 9 and 13.

Figure 14:
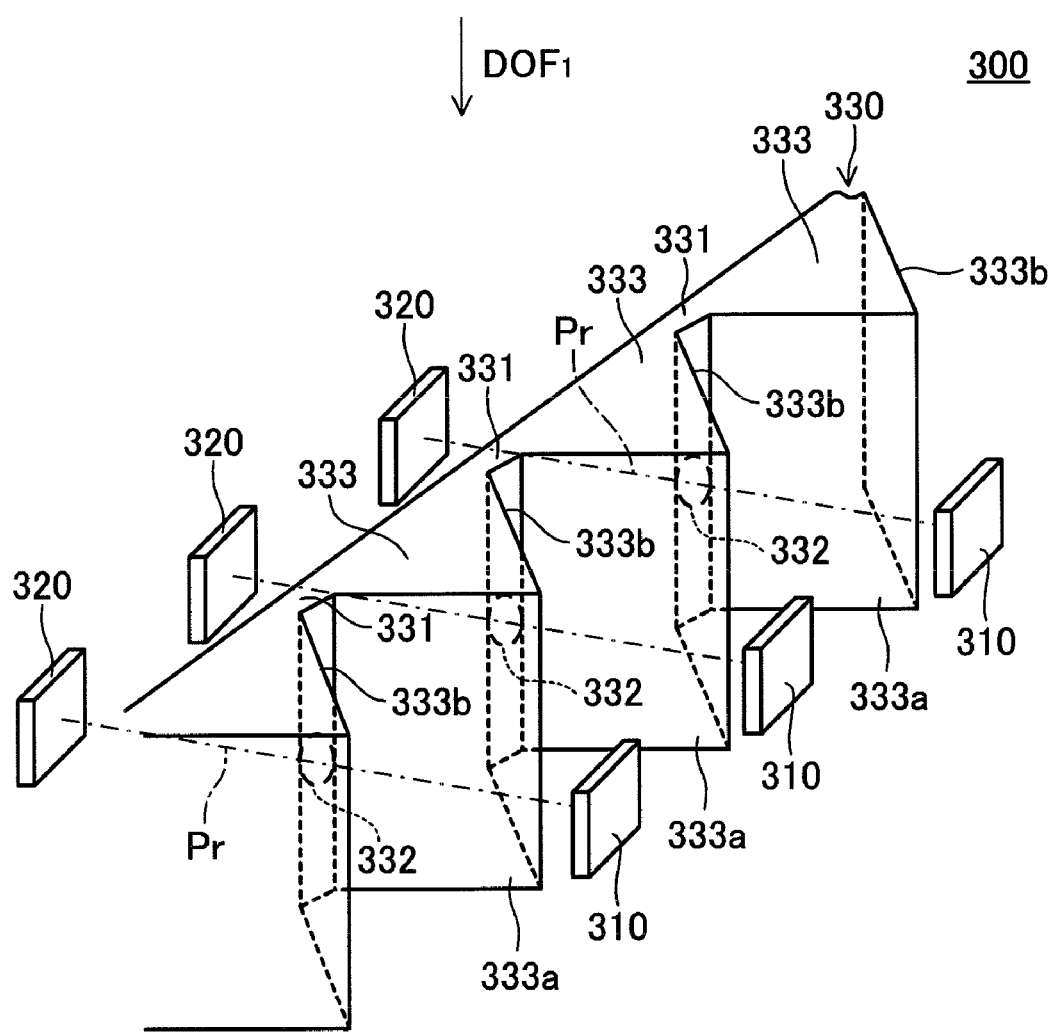
FIG. 14 is a perspective view showing a modification of the shielding member shown in FIG. 9 or 13.

(viii-1) FIG. 14 is a perspective view showing a modified configuration of the shielding member 330 shown in FIG. 9 or FIG. 13.

As shown in FIG. 14, the shielding member 330 may be composed of the shielding plates 331 and projections 333. Each of the projections 333 is formed to protrude along the direct vibration propagating route Pr from both ends of the shielding plate 331. The shielding plates 331 and the projections 333 are seamlessly and integrally formed.

In this modification, the projection 333 is formed into a triangle pole having a center axis generally parallel to the predetermined flight direction $DOF_1$. A first inclined face 333a and a second inclined face 333b, which are the surfaces facing the transmitting device 310, are provided so as to have an angle of 40 to 55 degrees made by the direct vibration propagating route Pr. The angle made by the first inclined face 333a and the direct vibration propagating route Pr and the angle made by the second inclined face 333b and the direct vibration propagating route Pr may be different from each other.

According to this configuration, the operation and an effect equal to those in the above-described embodiment can be obtained.

It is to be noted that, in the above-mentioned configuration, the shielding member 330 may have a wedge-like shape or flat plate shape.

Further, the shielding member 330 may be configured such that the first inclined face 333a and the second inclined face 333b are opposite to the receiving device 320.

Also, either one of the first inclined face 333a and the second inclined face 333b may have an angle of less than 40 degrees made by the direct vibration propagating route Pr.

Figure 15:
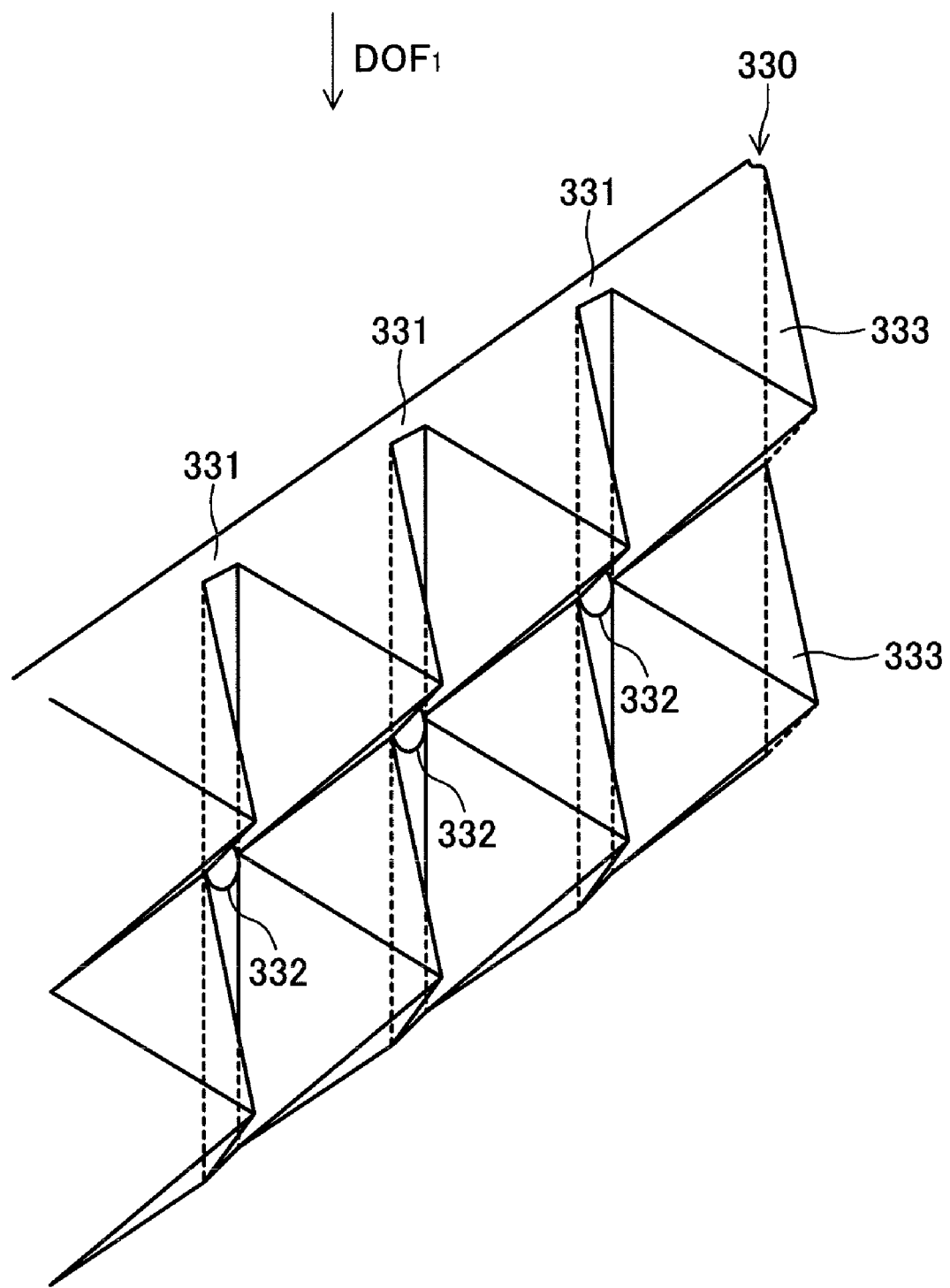
FIG. 15 is a perspective view showing another modification of the shielding member shown in FIG. 14.

(viii-2) FIG. 15 is a perspective view showing a modified configuration of the shielding member 330 shown in FIG. 14.

As shown in FIG. 15, the projection 333 may be divided into plural sections (two in FIG. 15) along the predetermined flight direction $DOF_1$. Specifically, the projection 333 may be constructed from a projection having a quadrangular pyramid shape and protruding from the shielding plate 331.

Figure 16:
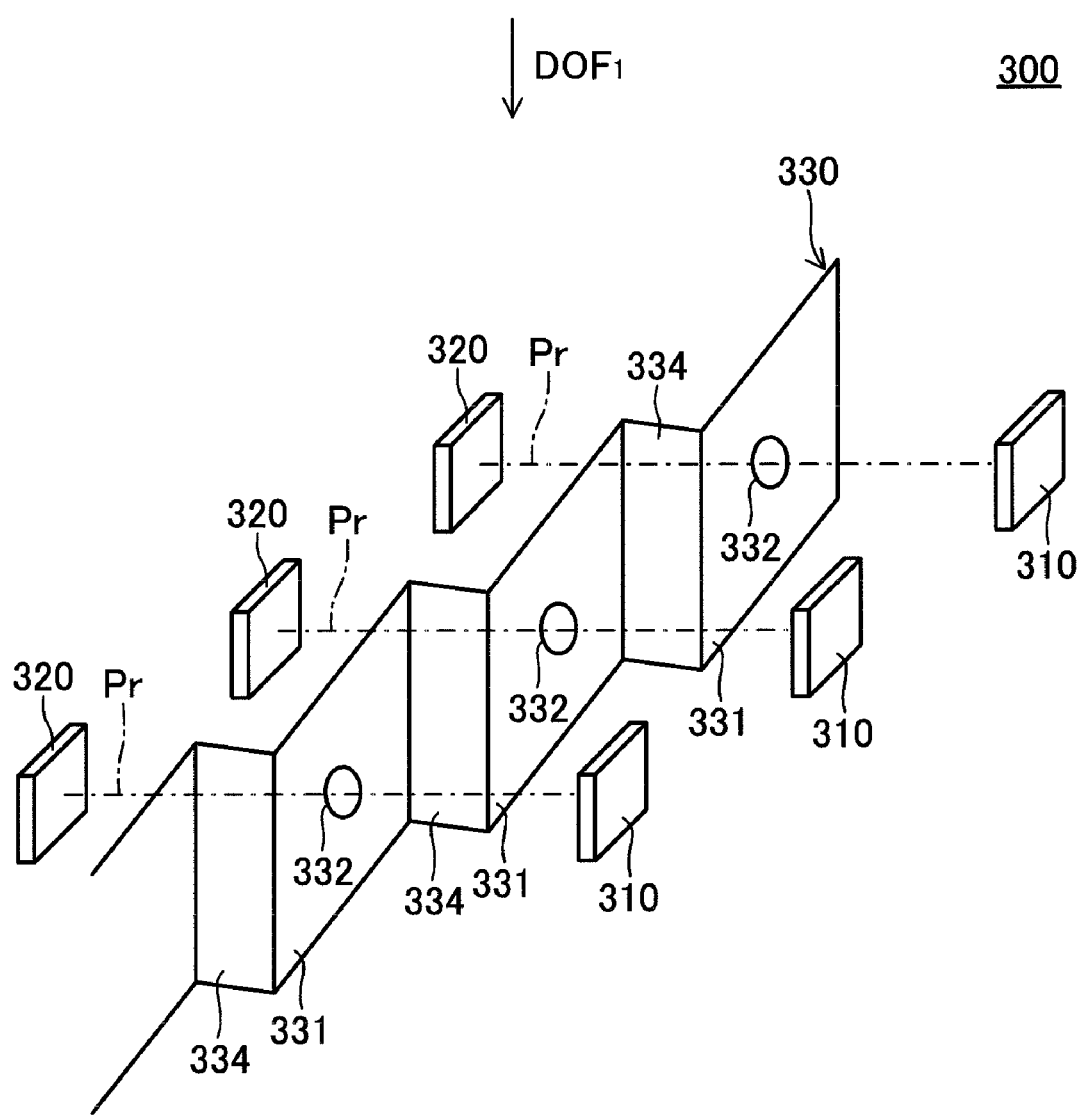
FIG. 16 is a perspective view showing another modification of the shielding member shown in FIG. 9 or 13.

(viii-3) FIG. 16 is a perspective view showing a modified configuration of the shielding member 330 shown in FIG. 9 or FIG. 13.

As shown in FIG. 16, the shielding plate 331 may be constructed from a thin plate member.

The shielding member 330 may also have plural shielding plates 331. In this case, the adjacent shielding plates 331 are joined by a joint plate 334. The shielding plate 331 is arranged in such a manner that its surface constitutes an inclined face in which the direction crossing the direct vibration propagating route Pr is defined as the normal. The shielding plates 331 and the joint plates 334 are seamlessly and integrally formed.

By virtue of this configuration, the construction in which the inclined faces face both of the transmitting device 310 and the receiving device 320 can very simply be realized.

Figure 17:
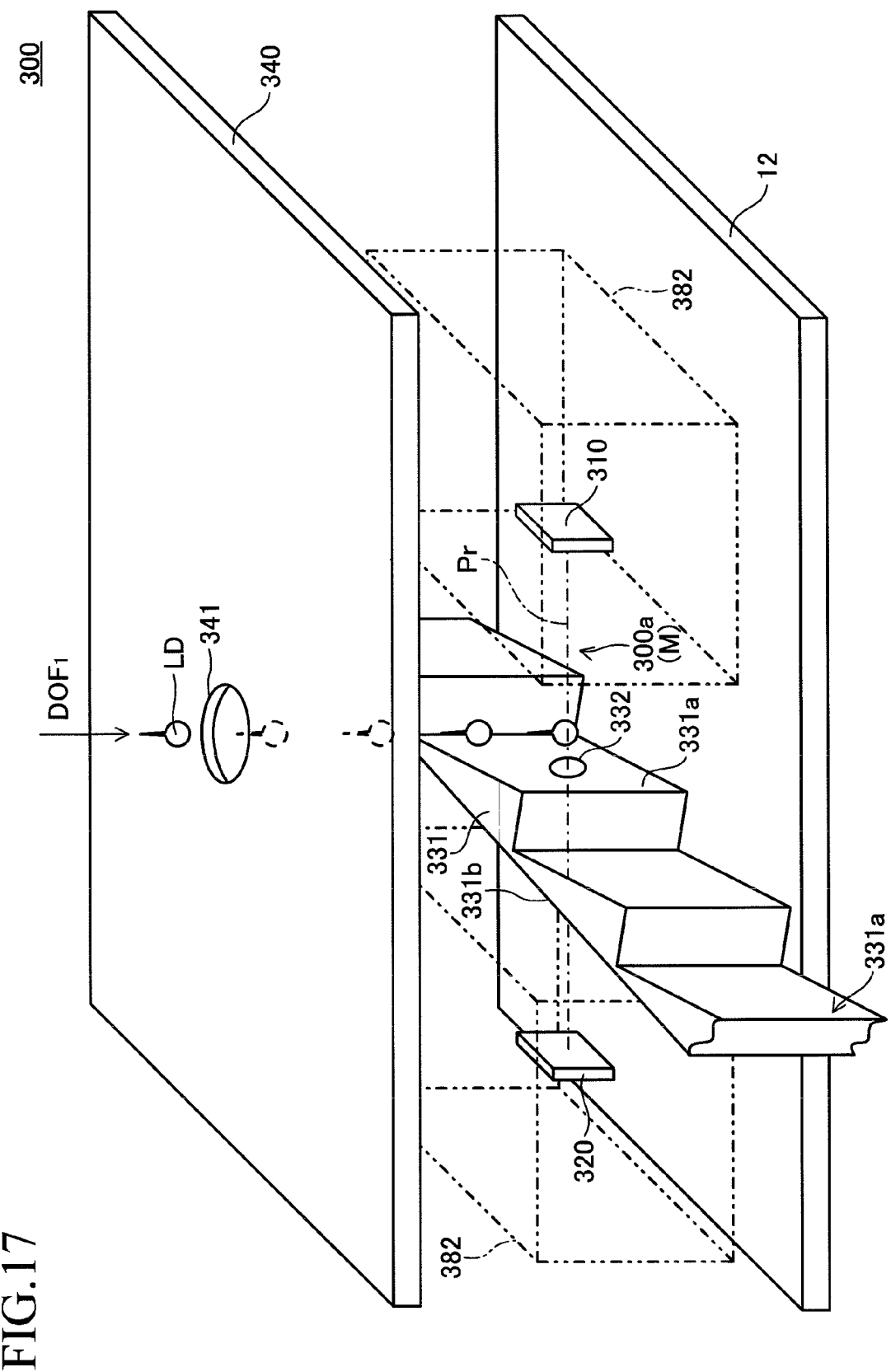
FIG. 17 is a perspective view showing another modification of the passage detection apparatus shown in FIG. 9.

(ix) FIG. 17 is a perspective view showing a configuration of the passage detection apparatus 300 shown in FIG. 9 according to another modification.

As shown in FIG. 17, a device noise reducing shield section 382 may be provided. This device noise reducing shield section 382 is provided to expose the portions of the transmitting device 310 and the receiving device 320, which are opposite to each other, and to cover the remaining portions in all directions.

According to this configuration, electrical noise to the transmitting device 310 and the receiving device 320 is eliminated by the device noise reducing shield section 382. Therefore, the S/N ratio for the object passage detection by the receiving device 320 is enhanced. Consequently, a more micro object can be detected with high precision.

It is to be noted that either one of the transmitting device 310 and the receiving device 320 (preferably the receiving device 320) may be shielded by the device noise reducing shield section 382.

Figure 18:
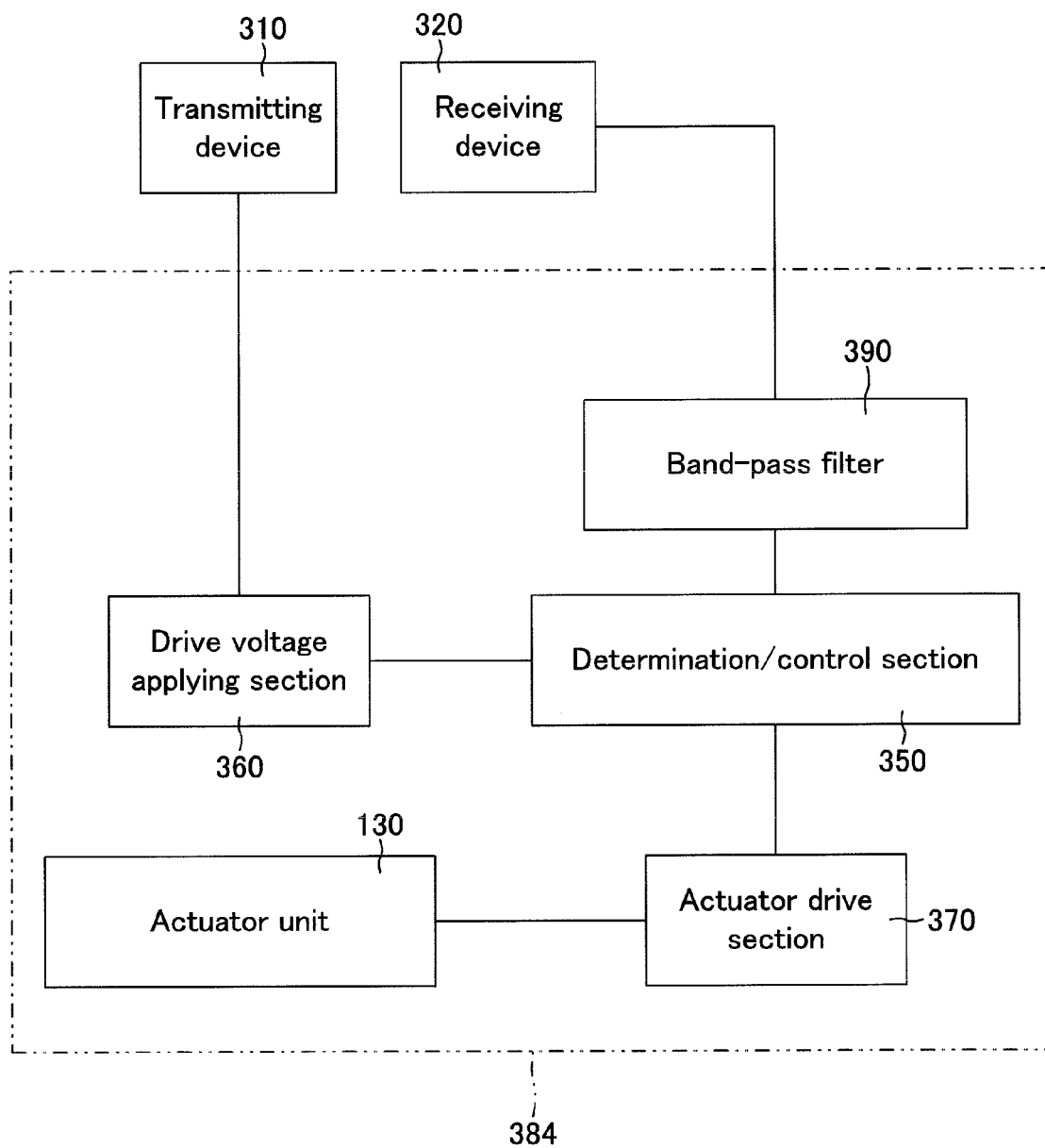
FIG. 18 is a block diagram showing one modification of the circuit construction shown in FIG. 11 for determining an ejecting state of a micro drop of a sample solution.

(x) FIG. 18 is a block diagram showing one modified example of the circuit construction shown in FIG. 11 for determining the ejection state of the micro drops of the sample solution.

As shown in FIG. 18, this circuit construction may be provided with a circuit noise reducing shield section 384. This circuit noise reducing shield section 384 is configured to cover the electric circuit, such as the determination/control section 350, etc., so as to eliminate electrical noise applied to the electric circuit.

According to this configuration, the electrical noise applied to the electric circuit such as the determination/control section 350 is eliminated by the circuit noise reducing shield section 384. Therefore, the S/N ratio for the object passage detection by the receiving device 320 is enhanced. Consequently, a more micro object can be detected with high precision.

(xi) It is to be noted that increasing sensitivity by the reduction of noise can be realized by employing at least one of the device noise reducing shield section 382 covering the transmitting device 310, the device noise reducing shield section 382 covering the receiving device 320, and the circuit noise reducing shield section 384. Further, it may suffice that the circuit noise reducing shield section 384 shields at least the determination/control section 350.

(xii) As shown in FIG. 18, a band-pass filter 390 may be provided in the circuit construction for determining the ejection state of the micro drops of the sample solution. The band-pass filter 390 may be interposed between the receiving device 320 and the determination/control section 350. This band-pass filter 390 is configured to restrict the frequency of the output from the receiving device 320 to the band (specifically, the range ±10% of the desired resonant frequency) in the vicinity of the desired resonant frequency.

With this configuration, a mechanical noise is eliminated that is based upon ambient sound wave, or the vibration or the like of an unnecessary mode other than the vibration of the desired mode corresponding to the desired resonant frequency. Accordingly, the S/N ratio for the object passage detection is enhanced. Consequently, a more micro object can be detected with high precision.

The band-pass filter 390 may be provided in the determination/control section 350.

(xiii) The constructions of the transmitting device 310 and the receiving device 320 are not limited to those described in the aforesaid embodiment.

Figure 19:
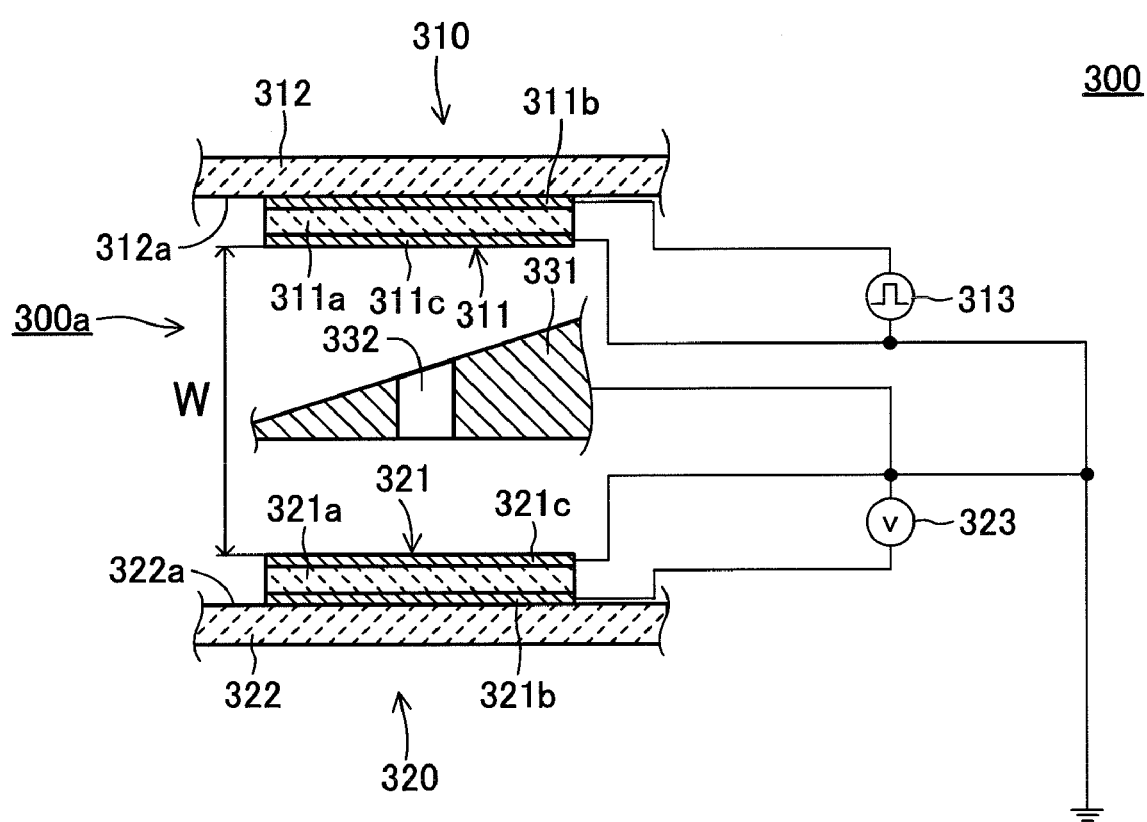
FIG. 19 is a sectional view showing one modification of the transmitting device and receiving device shown in FIG. 10.

(xiii-1) FIG. 19 is a sectional view showing one modification of the configurations of the transmitting device 310 and the receiving device 320 shown in FIG. 10.

In the configuration of the modification shown in FIG. 19, the first piezoelectric/electrostrictive element 311 is provided on the inner surface 312a of the first substrate 312. The second piezoelectric/electrostrictive element 321 is provided on the inner surface 322a of the second substrate 322. Specifically, the first piezoelectric/electrostrictive element 311 and the second piezoelectric/electrostrictive element 321 are arranged so as to face the specific space 300a.

By virtue of this configuration, the reception sensitivity of supersonic wave by the second piezoelectric/electrostrictive element 321 constituting the receiving device 320 can further be enhanced. Further, the passage detection apparatus 300 can further be downsized, and a drop having a more micro size can satisfactorily be detected.

(xiii-2) The mounting manner of the first piezoelectric/electrostrictive element 311 to the first substrate 312 and the mounting manner of the second piezoelectric/electrostrictive element 321 to the second substrate 322 can appropriately be changed from the manner described above.

For example, one of the piezoelectric/electrostrictive element 311 and the second piezoelectric/electrostrictive element 321 may be arranged to face the specific space 300a, and the other may be arranged at the outside of the specific space 300a.

The arrangement relationship between the transmitting device 310 and the first substrate 312 and between the receiving device 320 and the second substrate 322 can appropriately be selected depending upon the property of the micro drops of the sample solution (physical property such as volume, weight, electrical conductivity, charging amount, etc.; chemical property such as pH, corrosivity, etc.; moving speed; ejection cycle, and the like), the width of the specific space 300a (the distance between the inner surface 312a of the first substrate 312 and the inner surface 322a of the second substrate 322), the configurations of the transmitting device 310 and the receiving device 320, and other factors.

Figure 20:
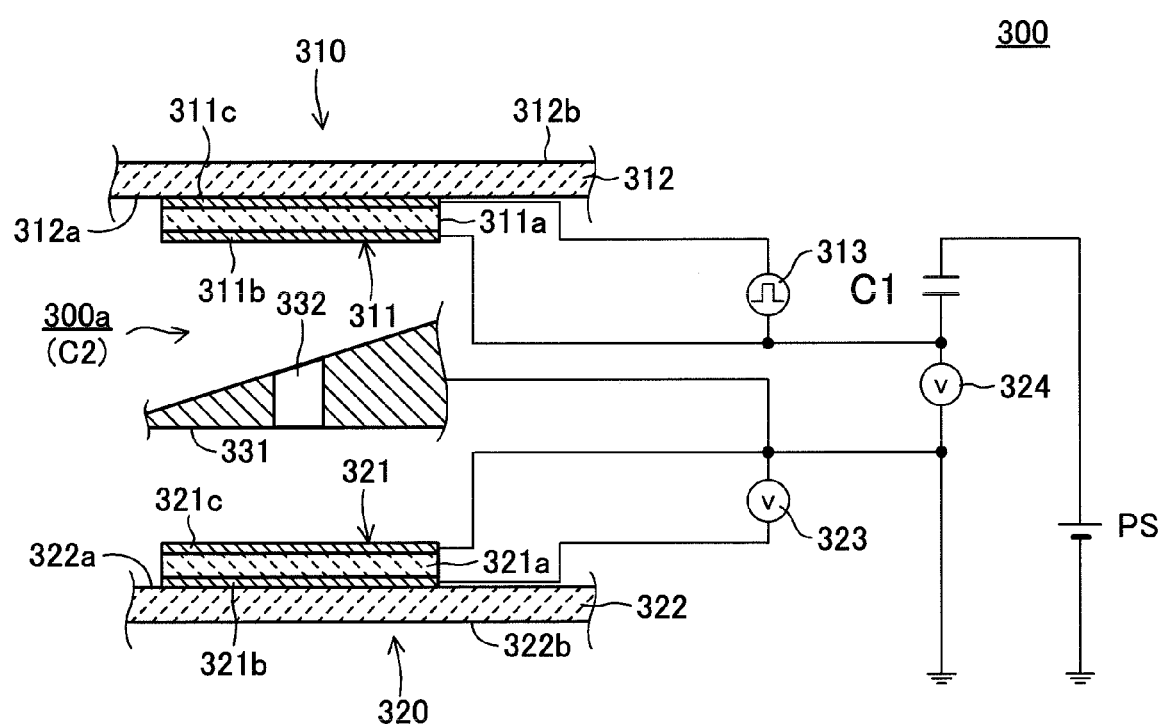
FIG. 20 is a sectional view showing another modification of the transmitting device and receiving device shown in FIG. 10.

(xiii-3) FIG. 20 is a sectional view showing one modification of the configurations of the transmitting device 310 and the receiving device 320 shown in FIG. 10.

The passage detection apparatus 300 according to this modification shown in FIG. 20 is configured to detect whether the micro drops of the sample solution pass through the specific space 300a or not and determine the volume of the micro drop, on the basis of the change in the dielectric constant in the specific space 300a (electrostatic capacity of a virtual capacitor) and the propagation state of the supersonic wave in the specific space 300a. The specific configuration of the passage detection apparatus 300 according to this modification will be described below.

In this modification, the pulse generating source 313 is connected to the first piezoelectric/electrostrictive element 311 constituting the transmitting device 310, like the configuration of the aforesaid embodiment. Further, the voltmeter 323 is connected to the second piezoelectric/electrostrictive element 321 constituting the receiving device 320.

The first piezoelectric/electrostrictive element 311 is arranged such that the drive electrode 311b is positioned at the side of the specific space 300a. This drive electrode 311b is connected to a DC power source PS through a known capacitor C1 having electrostatic capacitance. The second piezoelectric/electrostrictive element 321 is arranged such that the second reference electrode 321c is positioned at the side of the specific space 300a. The second reference electrode 321c is grounded together with the shielding plate 331.

The drive electrode 311b and the second reference electrode 321c are connected to the voltmeter 324 so as to acquire the voltage between both of them by the voltmeter 324. The voltmeter 323 is connected to the second piezoelectric/electrostrictive element 321 so as to acquire the voltage between the signal output electrode 321b and the second reference electrode 321c.

Specifically, in this modification, a virtual capacitor C2 is formed between the drive electrode 311b of the first piezoelectric/electrostrictive element 311, which is the electrode close to the specific space 300a, and the grounded shielding plate 331. The virtual capacitor C2 is configured to change its electrostatic capacitance according to the change in the dielectric constant in the specific space 300a (the presence of an object in the specific space 300a or the size of the object). Further, the virtual capacitor C2 is serially connected to the known capacitor C1. The voltmeter 324 acquires the partial pressure of the virtual capacitor C2 of the voltages of both ends of the DC power source PS.

As described above, the passage detection apparatus 300 according to the present modification is configured to determine whether the micro drop of the sample solution passes through the specific space 300a or not and the volume of the micro drop on the basis of the change in the partial pressure of the virtual capacitor C2, which is provided between the drive electrode 311b of the first piezoelectric/electrostrictive element 311 and the shielding plate 331, and the change in the output voltage from the second piezoelectric/electrostrictive element 321.

The circuit construction shown in FIG. 11 can also be used in this modification. In this case, the determination/control section 350 shown in FIG. 11 is configured to include the voltmeter 323, voltmeter 324, capacitor C1, and DC power source PS in FIG. 20.

In the configuration according to the present modification too, the drive control of the first piezoelectric/electrostrictive element 311 and the like is performed and the passage of the micro drops is determined as shown in FIG. 12 as described below by using the circuit construction shown in FIG. 11.

Referring to FIG. 20, when the first piezoelectric/electrostrictive element 311 constituting the transmitting device 310 is driven at a predetermined timing and a supersonic wave is generated. This supersonic wave propagates through the medium in the specific space 300a to reach the second substrate 322. Thus, the second substrate 322 is vibrated. A voltage is generated at the second piezoelectric/electrostrictive element 321 by the vibration of the second substrate 322. The voltage generated at the second piezoelectric/electrostrictive element 321 is acquired by the voltmeter 323.

The change in the partial pressure of the virtual capacitor C2 formed between the drive electrode 311b of the first piezoelectric/electrostrictive element 311 and the shielding plate 331 is acquired by the voltmeter 324. Whether or not the micro drop of the sample solution passes through the specific space 300a or the volume of the micro drop is determined on the basis of the outputs from the voltmeter 323 and the voltmeter 324. For example, when an appropriate statistical process is carried out by the determination/control section 350 in FIG. 11 to the result of the detection on the basis of the output from the voltmeter 323 and the result of the detection on the basis of the voltmeter 324, the passage of the object can be detected with higher reliability, regardless of the property of the object (size, chargeabililty, etc.).

The thickness of the shielding plate 331, the sectional shape thereof, and the position (the positional relationship with the first piezoelectric/electrostrictive element 311 and the second piezoelectric/electrostrictive element 321) can optionally be adjusted. Accordingly, the sensitivity in the passage detection of an object or stability can be enhanced.

Figure 21:
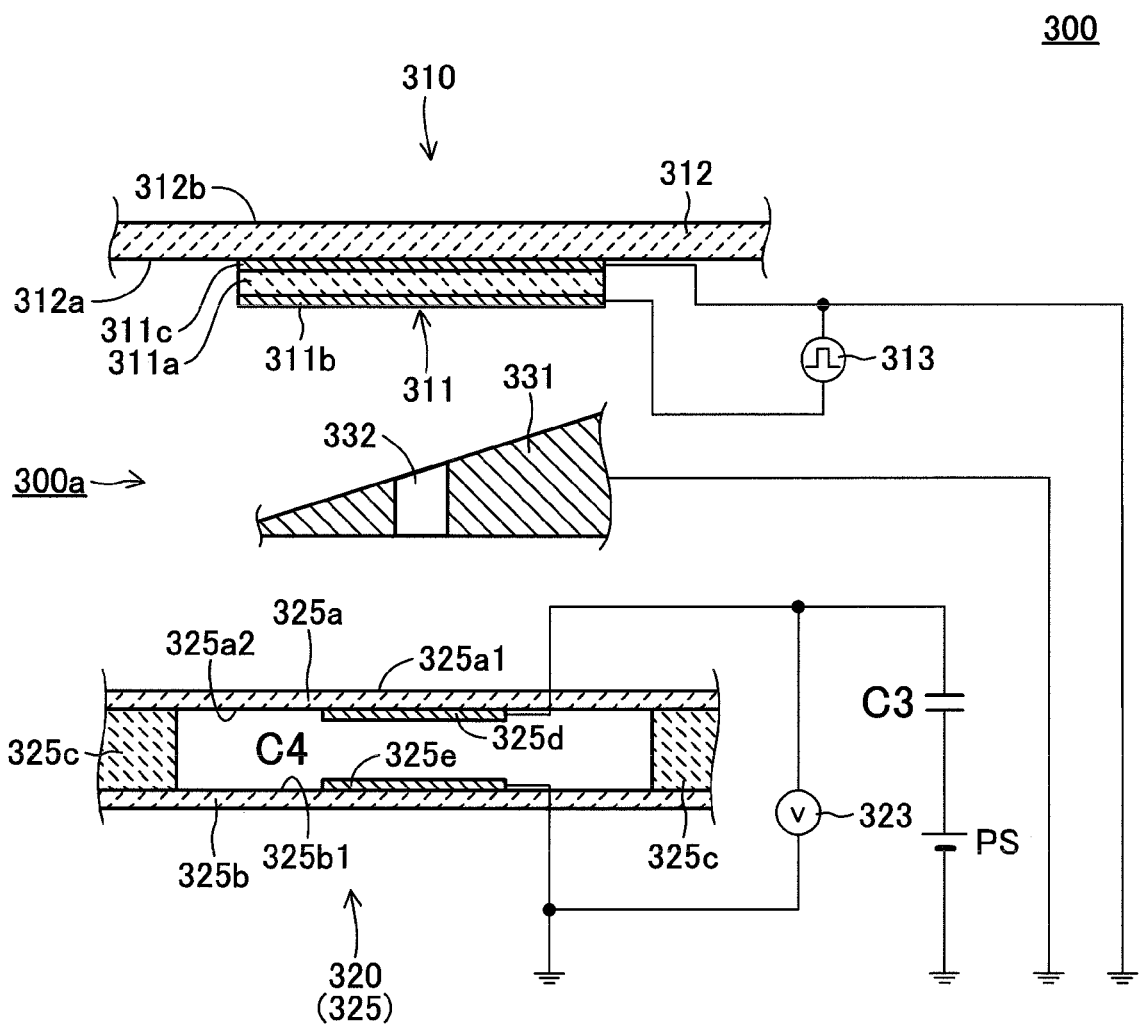
FIG. 21 is a sectional view showing another modification of the transmitting device and receiving device shown in FIG. 10.

(xiii-4) FIG. 21 is a sectional view showing another modification of the configuration of the transmitting device 310 and the receiving device 320 shown in FIG. 10.

In this modification, the transmitting device 310 is composed of the first piezoelectric/electrostrictive element 311 same as that in the aforesaid embodiment. On the other hand, the receiving device 320 is composed of an electrostatic microphone 325, different from the aforesaid embodiment.

The electrostatic microphone 325 has a vibrating plate 325a, support plate 325b, spacer 325c, first detection electrode 325d, and second detection electrode 325e, wherein a voltage according to applied external force is produced between the first detection electrode 325d and the second detection electrode 325e.

The vibrating plate 325a is made of a dielectric layer having a thin plate shape, and is a member for constituting the outer wall enclosing the specific space 300a (a member corresponding to the second substrate 322 [see FIG. 10] in the aforesaid embodiment). Specifically, the inner surface of the electrostatic microphone 325 facing the specific space 300a is made of the inner surface 325a1 of the vibrating plate 325a.

The support plate 325b is made of a dielectric layer having a thin plate shape. The support plate 325b is arranged so as to be parallel to the vibrating plate 325a with a predetermined gap. The spacer 325c is a plate-like member formed with multiple through-holes, and is arranged between the vibrating plate 325a and the support plate 325b so as to form a predetermined gap between the vibrating plate 325a and the support plate 325b by the through-holes.

As described above, the vibrating plate 325a is arranged to be bridged in the through-holes formed to the spacer 325c. The vibrating plate 325a is arranged at the position opposite to the first piezoelectric/electrostrictive element 311 serving as the vibration generating source. The vibrating plate 325a is configured to vibrate by the propagation of the vibration, generated from the first piezoelectric/electrostrictive element 311, through the medium in the specific space 300a.

The first detection electrode 325d is formed on the outer surface 325a2, which is the backside of the inner surface 325a1, of the vibrating plate 325a. The first detection electrode 325d is connected to the DC power source PS through a known capacitor C3 having electrostatic capacitance.

The second detection electrode 325e is formed on the inner surface 325b1, which faces the vibrating plate 325a, of the support plate 325b, and arranged parallel to the first detection electrode 325d. The second detection electrode 325e is grounded.

The first detection electrode 325d and the second detection electrode 325e are connected to the voltmeter 323 so as to acquire the voltage between both of them.

Specifically, a virtual capacitor C4 is formed in the electrostatic microphone 325 by the first detection electrode 325d and the second detection electrode 325e. The virtual capacitor C4 is configured to change its electrostatic capacitance depending upon the change in the distance of the gap, caused by the vibration of the vibrating plate 325a, between the first detection electrode 325d and the second detection electrode 325e. The virtual capacitor C4 is serially connected to the aforesaid known capacitor C3. The voltmeter 323 is connected to the first detection electrode 325d and the second detection electrode 325e in such a manner that the partial pressure of the virtual capacitor C4, of the voltages at both ends of the DC power source PS, can be acquired by the voltmeter 323.

As described above, the electrostatic microphone 325 in this modification is configured to output an signal according to the vibrating state of the vibrating plate 325a on the basis of the change in the partial pressure of the virtual capacitor C4. The passage detection apparatus 300 in the present modification is configured to determine whether the micro drop of the sample solution passes through the specific space 300a or the volume of the micro drop, through the detection of the propagation state of the supersonic wave in the specific space 300a on the basis of the change in the voltage at both ends of the voltmeter 323.

In the present modification too, the circuit construction shown in FIG. 11 can be used. In this case, the determination/control section 350 in FIG. 11 is configured to include the voltmeter 323, capacitor C3, and DC power source PS in FIG. 21.

The operation of the determination of the object passage according to the configuration of the present modification will be explained with reference to the drawings.

Referring to FIG. 21, when the first piezoelectric/electrostrictive element 311 constituting the transmitting device 310 is driven at a predetermined timing, supersonic wave is generated.

In the present modification, the vibrating plate 325a vibrates due to the supersonic wave propagated to the receiving device 320 through the medium in the specific space 300a. The distance of the gap between the first detection electrode 325d and the second detection electrode 325e changes (specifically, the electrostatic capacitance of the virtual capacitor C4 changes) by the vibration of the vibrating plate 325a. With the change of the electrostatic capacitance of the virtual capacitor C4, the change in the partial pressure of the virtual capacitor C4 is acquired by the voltmeter 323. The state of the change in the partial pressure varies depending upon whether the micro drop enters the specific space 300a or not and the size of the micro drop as shown in FIG. 12(c). Consequently, whether the micro drop enters the specific space 300a or not and the size of the micro drop can be determined.

According to the configuration of the present modification, various materials can be selected as the material for the vibrating plate 325a. For example, a film made of synthetic resin may be used as the vibrating plate 325a. In this case, the first detection electrode 325d can also be formed easily into a thin film by the application of a metallized film. Accordingly, the whole rigidity of the vibrating plate 325a and the first detection electrode 325d reduces, whereby the vibrating plate 325a greatly vibrates due to a slight vibration of the medium in the specific space 300a. Therefore, the slight change of the vibration state of the medium can appear as the great change of the vibration state at the vibrating plate 325a. Consequently, the sensitivity in detecting a passage of an object can further be enhanced.

Figure 22:
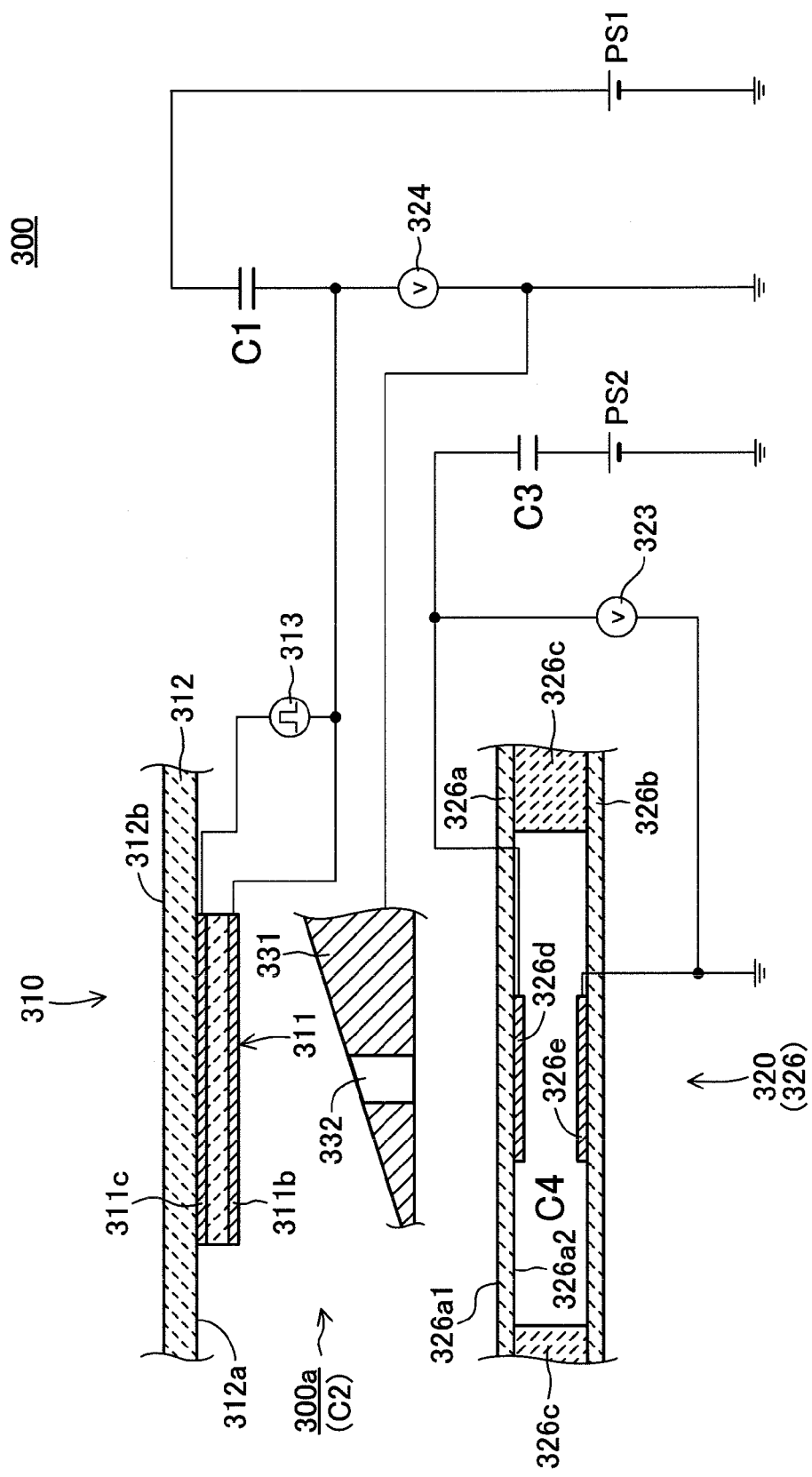
FIG. 22 is a sectional view showing another modification of the transmitting device and receiving device shown in FIG. 10.

(xiii-5) FIG. 22 is a sectional view showing a configuration of the transmitting device 310 and the receiving device 320 shown in FIG. 10 according to another modification.

The passage detection apparatus 300 in this modification has a configuration in which the configuration of the modification shown in FIG. 20 and the configuration of the modification shown in FIG. 21 are combined.

Specifically, like the modification shown in FIG. 20, the passage detection apparatus 300 according to the present modification is configured to determine whether the micro drop of the sample solution passes through the specific space 300a or not and the volume of the micro drop on the basis of the change in the electrostatic capacitance in the specific space 300a and the propagating state of the supersonic wave in the specific space 300a. The passage detection apparatus 300 in the present modification has the configuration same as that of the modification shown in FIG. 20, except that an electrostatic microphone 326 is used instead of the second piezoelectric/electrostrictive element 321 (see FIG. 20), and the construction of the electric circuit involved with the electrostatic microphone 326 is slightly different.

Specifically, the first piezoelectric/electrostrictive element 311 is arranged such that the drive electrode 311b is positioned at the side of the specific space 300a. The drive electrode 311b is connected to a DC power source PS1 through a known capacitor C1 having electrostatic capacitance. A pulse generating source 313 is connected to the drive electrode 311b and the first reference electrode 311c.

The electrostatic microphone 326 in the present modification has a vibrating plate 326a, support plate 326b, spacer 326c, first detection electrode 326d, and second detection electrode 326e, those of which are equal respectively to the vibrating plate 325a, support plate 325b, spacer 325c, first detection electrode 325d, and second detection electrode 325e of the electrostatic microphone 325 in FIG. 21. The first detection electrode 326d is connected to a DC power source PS2 through a known capacitor C3 having electrostatic capacitance. The second detection electrode 326e is grounded.

The shielding plate 331 is arranged between the first piezoelectric/electrostrictive element 311 and the inner surface 326a1 of the electrostatic microphone 326. This shielding plate 331 is grounded.

The first detection electrode 325d and the second detection electrode 325e are connected to the voltmeter 323. The shielding plate 331 and the drive electrode 311*b* of the first piezoelectric/electrostrictive element 311 are connected to the voltmeter 324.

As described above, the passage detection apparatus 300 in the present modification is configured to determine whether or not the micro drop of the sample solution passes through the specific space 300*a* or the volume of the micro drop, on the basis of the change in the partial pressure of the virtual capacitor C2 in the serial circuit made of the known capacitor C1 and the virtual capacitor C2, and the change in the partial pressure of the virtual capacitor C4 in the serial circuit made of the known capacitor C3 and the virtual capacitor C4 formed by the electrostatic microphone 326.

In the configuration according to the present modification too, the drive control of the first piezoelectric/electrostrictive element 311 and the like is performed and the passage of the micro drops is determined as shown in FIG. 12 as described below by using the circuit construction shown in FIG. 11.

Referring to FIG. 22, when the first piezoelectric/electrostrictive element 311 constituting the transmitting device 310 is driven at a predetermined timing, supersonic wave is generated. This supersonic wave propagates through the medium in the specific space 300*a* to reach the vibrating plate 326*a*. Thus, the vibrating plate 326*a* is vibrated. The distance of the gap between the first detection electrode 326*d* and the second detection electrode 326*e* is changed (specifically, the electrostatic capacity of the virtual capacitor C4 is changed) by the vibration of the vibrating plate 326*a*. With the change in the electrostatic capacitance of the virtual capacitor C4, the partial pressure generated at both ends of the virtual capacitor C4 in the serial circuit made of the virtual capacitor C4 and the known capacitor C3 changes. Specifically, the voltage generated at the electrostatic microphone 326 changes. The voltage generated at the electrostatic microphone 326 is acquired by the voltmeter 323.

The change in the partial pressure of the virtual capacitor C2 formed between the drive electrode 311*b* of the first piezoelectric/electrostrictive element 311 and the shielding plate 331 is acquired by the voltmeter 324. Whether or not the micro drop of the sample solution passes through the specific space 300*a* or the volume of the micro drop is determined on the basis of the outputs from the voltmeter 323 and the voltmeter 324. For example, when an appropriate statistical process is carried out by the determination/control section 350 in FIG. 11 based on the result of the detection on the basis of the output from the voltmeter 323 and the result of the detection on the basis of the voltmeter 324, the passage of the object can be detected with higher reliability, regardless of the property of the object (size, chargeabililty, etc.).

Figure 23:
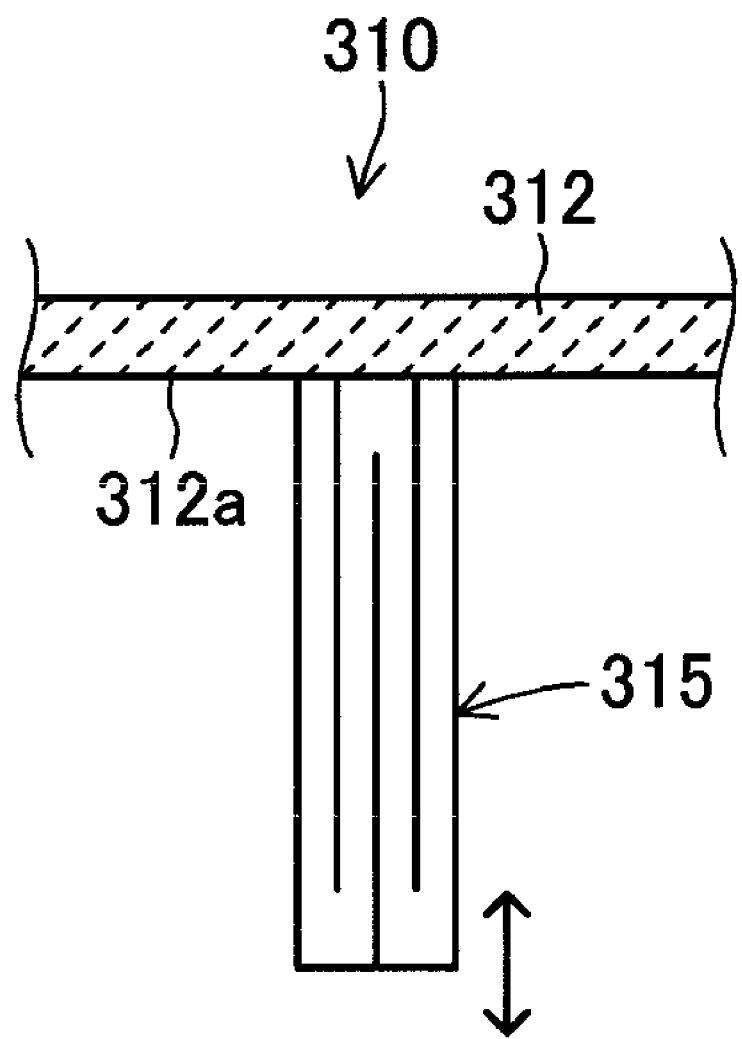
FIG. 23 is a sectional view showing another modification of the transmitting device shown in FIG. 10.

(xiii-6) FIG. 23 is a sectional view showing configurations of the transmitting device 310 shown in FIG. 10 according to another modification.

A multi-layer piezoelectric/electrostrictive element 315 shown in FIG. 23 can be applied as the vibration generating source in the transmitting device 310. Accordingly, the intensity of the generated supersonic wave is enhanced, and the passage detection with higher reliability can be carried out.

Figure 24:
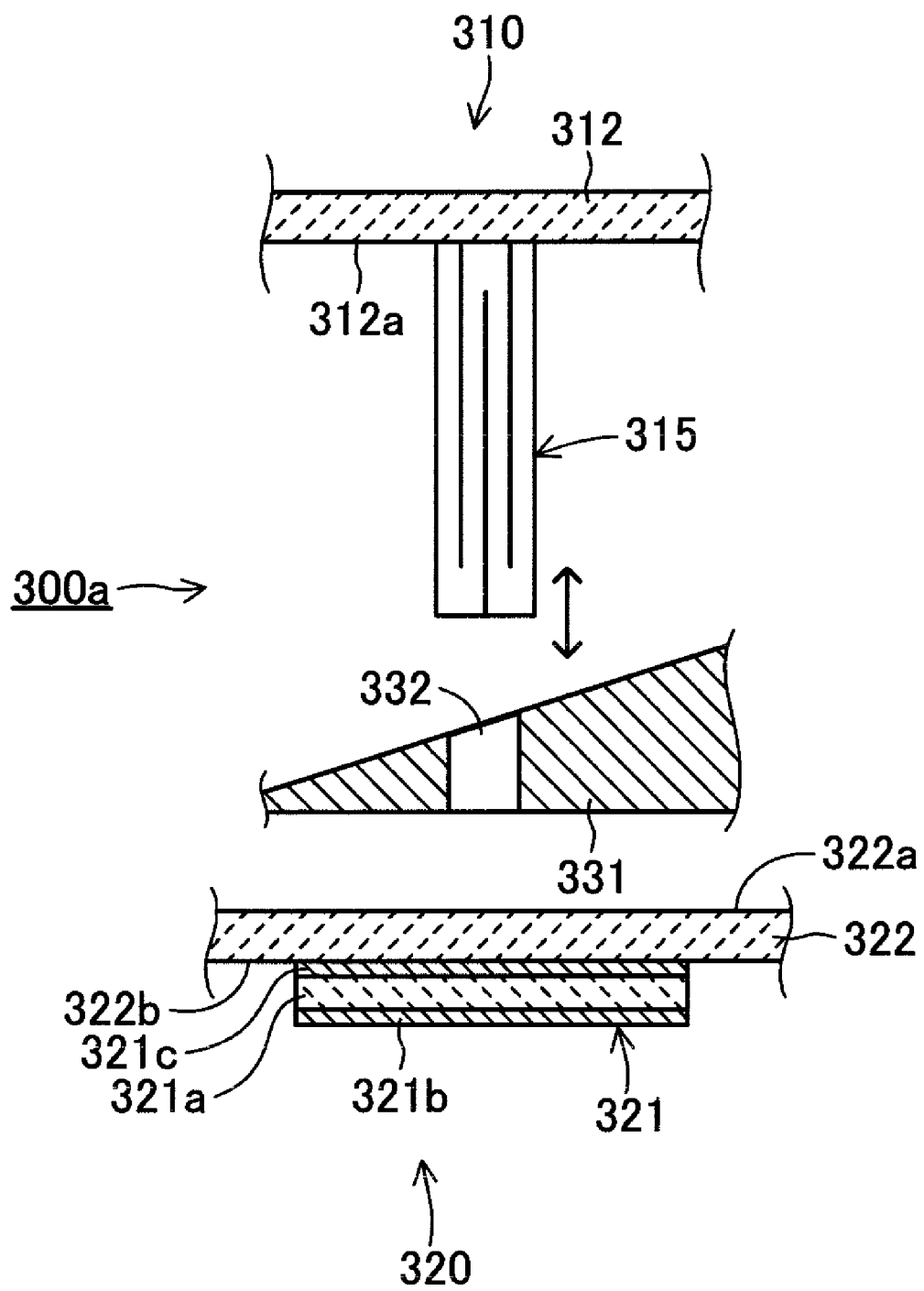
FIG. 24 is a perspective view showing a modification of a passage detection apparatus provided with the transmitting device shown in FIG. 23.

In this case, the multi-layer piezoelectric/electrostrictive element 315 constituting the vibration generating source in the transmitting device 310 is different from the receiving device 320 as illustrated in FIG. 24. Even if the primary resonant frequencies of the transmitting device 310 and the receiving device 320 are equal to each other, the high-order resonant frequencies of both of them are different from each other.

In this configuration, the output from the receiving device 320 on the basis of the vibration other than the desired vibration mode in the transmitting device 310 is suppressed. Therefore, the S/N ratio in detecting the passage of an object is enhanced. Accordingly, a detection of a more micro object becomes possible with this configuration.

(xiv) Referring to FIG. 10, various constructions can be employed for the first substrate 312 of the transmitting device 310.

Figure 25:
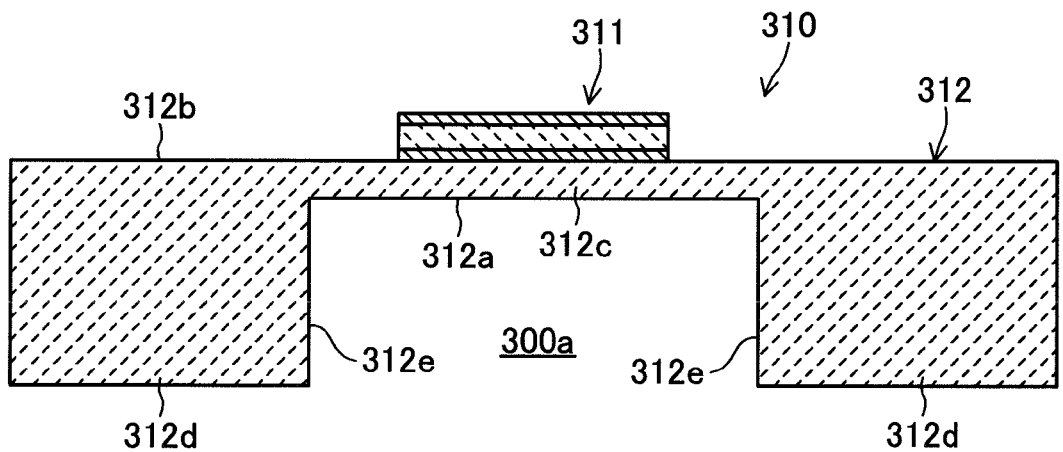
FIG. 25 is a sectional view showing a modification of the first substrate shown in FIG. 10.

FIG. 25 is a sectional view showing a configuration of the first substrate 312 shown in FIG. 10 according to one modification. FIG. 25 illustrates the configuration in which the first piezoelectric/electrostrictive element 311 is attached to the first substrate 312 of the modification. It is not necessary to mention that the present modification is not limited to the configuration described above (that the multiple-layer piezoelectric/electrostrictive element 315 can be used instead of the first piezoelectric/electrostrictive element 311, for example).

As shown in FIG. 25, the first substrate 312 includes a diaphragm 312*c* having a thin flat-plate shape, and a diaphragm support thick part 312*d* of a flat plate type formed at both sides of the diaphragm 312*c*. The diaphragm support thick part 312*d* is made of a material same as the material of the diaphragm 312*c*, and formed so as to be thicker than the diaphragm 312*c*. The diaphragm 312*c* and the diaphragm support thick part 312*d* are seamlessly and integrally formed. A vibration generating source (first piezoelectric/electrostrictive element 311) is attached to the diaphragm 312*c*.

In this configuration, the first substrate 312 in the present modification is configured such that the diaphragm 312*c* is bridged between the adjacent diaphragm support thick parts 312*d*. Therefore, the vibration can be generated from the transmitting device 310 with high output.

As shown in FIG. 25, the outer surface 312*b* of the first substrate 312 in the present modification is composed of the outer surfaces of the diaphragm 312*c* and the diaphragm support thick part 312*d*. Specifically, the first substrate 312 in the present modification is configured such that the outer surface of the diaphragm 312*c* and the outer surface of the diaphragm support thick part 312*d* are continuous on the same plane.

The first substrate 312 is also configured such that the space (the space inside a recess portion formed at the side of the inner surface 312*a* of the first substrate 312) enclosed by the inner surface 312*a* of the first substrate 312 composed of the inner surface of the diaphragm 312*c* and the cavity side face 312*e* of the diaphragm support thick part 312*d* is included in the specific space 300*a*.

In this configuration, the aforesaid recess portion constituting the specific space 300*a* is formed at the side of the inner surface 312*a* of the first substrate 312. Therefore, a part of the specific space 300*a* can be constructed within the range of the thickness of the first substrate 312. Accordingly, the passage detection apparatus can be downsized.

The cavity side face 312*e* of the diaphragm support thick part 312*d* shown in FIG. 25 may be configured to reflect sound wave or supersonic wave.

In this configuration, sound wave or supersonic wave is reflected with high efficiency by the cavity side face 312*e* of the diaphragm support thick part 312*d*, which constitutes the inner wall face of the aforesaid recess portion forming the specific space 300*a*. Accordingly, the directivity upon the propagation of the sound wave or supersonic wave through the medium in the specific space 300*a* is enhanced. Consequently, even if the output from the vibration generating source (first piezoelectric/electrostrictive element 311) is decreased to reduce power consumption, the detection of the passage is satisfactorily performed.

Although FIG. 25 illustrates as the vibration generating source (the first piezoelectric/electrostrictive element 311) is attached to the outer surface 312b of the first substrate 312 (diaphragm 312c), the present modification is not limited thereto. The vibration generating source (first piezoelectric/electrostrictive element 311) may be attached to the inner surface 312a of the first substrate 312 (diaphragm 312c).

(xv) Referring to FIG. 10, various constructions can be employed for the second substrate 322 of the receiving device 320.

Figure 26:
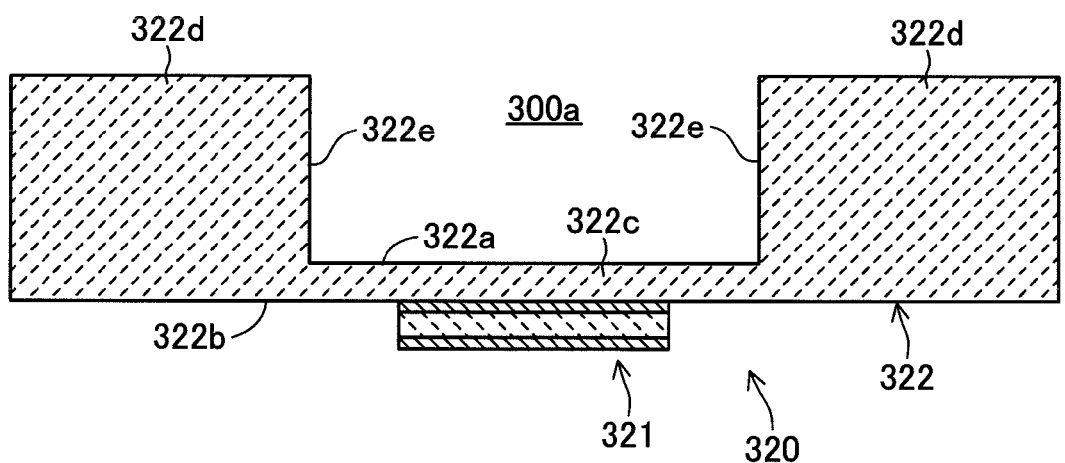
FIG. 26 is a sectional view showing a modification of the second substrate shown in FIG. 10.

FIG. 26 is a sectional view showing a configuration of the second substrate 322 shown in FIG. 10 according to one modification. FIG. 26 illustrates the configuration in which the second piezoelectric/electrostrictive element 321 is attached to the second substrate 322 of the modification. It is not necessary to mention that this modification is not limited to the configuration described above (that the electrostatic microphone 325 in FIG. 21 or the electrostatic microphone 326 in FIG. 22 can be used, for example).

As shown in FIG. 26, the second substrate 322 includes a diaphragm 322c having a thin flat-plate shape, and a diaphragm support thick part 322d of a flat plate type formed at both sides of the diaphragm 322c. The diaphragm support thick part 322d is made of a material same as the material of the diaphragm 322c, and formed so as to be thicker than the diaphragm 322c. The diaphragm 322c and the diaphragm support thick part 322d are seamlessly and integrally formed. A signal generating section that constitutes a main part of the receiving device 320, such as the second piezoelectric/electrostrictive element 321, etc., is attached to the diaphragm 322c.

In this configuration, the second substrate 322 in the present modification is configured such that the diaphragm 322c is bridged between the adjacent diaphragm support thick parts 322d. Therefore, the diaphragm 322c can be vibrated with high efficiency due to the vibration propagated through the medium in the specific space 300a. Accordingly, the reception of the vibration by the receiving device 320 is performed with high sensitivity, whereby a passage of an object can be detected with high sensitivity.

As shown in FIG. 26, the outer surface 322b of the second substrate 322 in the present modification is composed of the outer surfaces of the diaphragm 322c and the diaphragm support thick part 322d. Specifically, the second substrate 322 in the present modification is configured such that the outer surface of the diaphragm 322c and the outer surface of the diaphragm support thick part 322d are continuous on the same plane. The second substrate 322 is also configured such that the space (the space inside a recess portion formed at the side of the inner surface 322a of the second substrate 322) enclosed by the inner surface 322a of the second substrate 322 composed of the inner surface of the diaphragm 322c and the cavity side face 322e of the diaphragm support thick part 322d is included in the specific space 300a.

In this configuration, the aforesaid recess portion constituting the specific space 300a is formed at the side of the inner surface 322a of the second substrate 322. Therefore, a part of the specific space 300a can be constructed within the range of the thickness of the second substrate 322. Accordingly, the passage detection apparatus can be downsized.

The cavity side face 322e of the diaphragm support thick part 322d shown in FIG. 26 may be configured to reflect sound wave or supersonic wave.

In this configuration, sound wave or supersonic wave is reflected with high efficiency by the cavity side face 322e of the diaphragm support thick part 322d, which constitutes the inner wall face of the aforesaid recess portion forming the specific space 300a. Accordingly, the directivity upon the propagation of the sound wave or supersonic wave through the medium in the specific space 300a is enhanced.

Although FIG. 26 illustrates as the signal generating section is attached to the outer surface 322b of the second substrate 322 (diaphragm 322c), the present modification is not limited thereto. The signal generating section may be attached to the inner surface 322a of the second substrate 322 (diaphragm 322c).

(xvi) The known capacitors C1 and C3 in FIGS. 20 to 22 can be replaced by a resistor. In addition, an optional circuit construction can be employed for the circuit constructions shown in the aforesaid respective drawings.

(xvii) The vibration plate 325a and the support plate 325b in FIG. 21 may be made of a conductive material. With this configuration, the functions of the first detection electrode 325d and the second detection electrode 325e can be given to the vibrating plate 325a and the support plate 325b.

(xviii) In addition, the respective components constituting the means to solve the problems of the present invention, particularly, the components which are expressed operatively and functionally, include all structures that can be operatively and functionally realized in addition to the clearly defined structures disclosed in the above-described embodiments and modifications.

What is claimed is:

1. A passage detection apparatus for an object capable of detecting a passage of an object in a specific space, the passage detection apparatus comprising:
   a transmitting device provided with a vibration generating source;
   a receiving device that is arranged at the position corresponding to the transmitting device across the specific space and can generate an output according to a vibration, which is transmitted from the transmitting device to propagate through a medium in the specific space, wherein the receiving device comprising a reference electrode set to a predetermined potential and a signal output electrode whose potential varies on the bases of the vibration and of whether the object passes or not; and
   a shielding member that is formed with a through-hole formed between the transmitting device and the receiving device so as to face a route through which the object passes, and that is arranged so as to be interposed between the transmitting device and the receiving device, wherein the shielding member is set to have the same potential as that of the reference electrode.

2. A passage detection apparatus according to claim 1, wherein the shielding member is configured to have an inclined face in which a direction crossing a direct vibration propagating direction, which is a direction of linking the transmitting device and the receiving device, is defined as the normal.

3. A passage detection apparatus according to claim 1, wherein on the assumption that the circle-equivalent diameter of the through-hole is defined as d1, the circle-equivalent diameter of the object is defined as d2, the average speed of the object at the through-hole is defined as v, and the cycle of the vibration is defined as T, the passage detection apparatus may be configured to satisfy the following inequalities:

$$d2^2/d1^2 \geq 0.6, (d1-d2)/v \geq 3T.$$

4. A passage detection apparatus according to claim 1, wherein
   the transmitting device and the receiving device are configured such that the resonant frequency of the transmitting device and the resonant frequency of the receiving device are generally the same in a first vibration mode, and the resonant frequency of the transmitting device and the resonant frequency of the receiving device are different from each other at a second vibration mode that is different from the first vibration mode.

5. A passage detection apparatus according to claim 1, further comprising:
a determining section that determines the passage of the object in the specific space on the basis of the output from the receiving device; and a device noise reducing shield section that is provided so as to cover the transmitting device and/or receiving device, and/or a circuit noise reducing shield section that is configured to cover the determining section for eliminating electrical noise applied to the determining section.

6. A passage detection apparatus according to claim 1, further comprising:

a band-pass filter that is configured to limit the frequency of the output from the receiving device to a band in the vicinity of a predetermined resonant frequency.

7. A passage detection apparatus according to claim 1, further comprising:
an aperture plate of a flat-plate type that is arranged at an end portion which is the side of the inlet for the object of the specific space so as to cross the passing direction of the object, wherein the aperture plate is formed with an aperture, which is a through-hole through which the object can pass and the aperture is formed smaller than the size of the specific space at the section perpendicular to the passing direction of the object.

* * * * *